United States Patent
Briere et al.

(10) Patent No.: US 12,336,820 B2
(45) Date of Patent: Jun. 24, 2025

(54) METHODS OF PREPARING/OPTIMIZING PERFUME COMPOSITIONS

(71) Applicant: GIVAUDAN SA, Vernier (CH)

(72) Inventors: Thomas Briere, Paris (FR); Julia Brooks, Ashford (GB); Ioannis Kontaris, Ashford (GB); Kristopher George Magee, Bristol (GB); Christopher Pley-Dell-Pearce, Bristol (GB)

(73) Assignee: GIVAUDAN SA, Vernier (CH)

(*) Notice: Subject to any disclaimer, the term of this patent is extended or adjusted under 35 U.S.C. 154(b) by 656 days.

(21) Appl. No.: 17/619,646

(22) PCT Filed: May 1, 2020

(86) PCT No.: PCT/EP2020/062178
§ 371 (c)(1),
(2) Date: Dec. 16, 2021

(87) PCT Pub. No.: WO2020/165463
PCT Pub. Date: Aug. 20, 2020

(65) Prior Publication Data
US 2022/0334094 A1    Oct. 20, 2022

(30) Foreign Application Priority Data
Jun. 27, 2019 (GB) ...................... 1909221

(51) Int. Cl.
*A61B 5/16* (2006.01)
*C11B 9/00* (2006.01)
*A61M 21/00* (2006.01)

(52) U.S. Cl.
CPC ............... *A61B 5/165* (2013.01); *C11B 9/00* (2013.01); *C11B 9/0007* (2013.01); *C11B 9/0061* (2013.01); *A61M 2021/0016* (2013.01)

(58) Field of Classification Search
CPC .................................. A61B 5/16; C11B 9/00
USPC ............................................................ 512/1
See application file for complete search history.

(56) References Cited

U.S. PATENT DOCUMENTS

| 6,114,300 A | 9/2000 | Bourdin et al. |
| 2009/0136436 A1 | 5/2009 | Bara |
| 2011/0092604 A1 | 4/2011 | Woehrle et al. |
| 2018/0051231 A1 | 2/2018 | Kontaris et al. |

FOREIGN PATENT DOCUMENTS

| CN | 1845983 A | 10/2006 | |
| EP | 1343466 A1 | 9/2003 | |
| EP | 1661973 A | 5/2006 | |
| EP | 1661973 A1 | 5/2006 | |
| EP | 1898865 B1 | 4/2010 | |
| EP | 2807925 A1 | 12/2014 | |
| RU | 2375042 C1 | 12/2009 | |
| RU | 2669029 C1 | 11/2014 | |
| WO | 02049600 A1 | 6/2002 | |
| WO | 2006136828 A1 | 12/2006 | |
| WO | 2016074697 A1 | 5/2016 | |
| WO | 2017015315 A1 | 1/2017 | |
| WO | 2018002298 A1 | 1/2018 | |
| WO | WO-2018206297 A1 * | 11/2018 | ............. A61K 8/022 |

OTHER PUBLICATIONS

International Search Report and Written Opinion of the International Searching Authority for corresponding application PCT/EP2020/062178 dated Aug. 25, 2020.
GB Search Report for corresponding GB application 1209221.2 dated Dec. 23, 2019.
RU Search Report for corresponding application RU 2021137561/04, with English language translation, dated Feb. 5, 2024.
Agapov E.P.; "Phenomenon of human well-being"; Medico-social and psychological aspects of industrial agglomerations safety: International Scientific and Practical Conference, Ekaterinburg], pp. 216-223, [ найдено онлайн найдено May 2, 2024], found in Internet: https://elar.urfu.ru/handle/10995/38037, pp. 216-217, with English language extract.

* cited by examiner

*Primary Examiner* — Jessica Whiteley
(74) *Attorney, Agent, or Firm* — Norris McLaughlin, PA

(57) ABSTRACT

A method of assessing the impact of a test perfume composition on the well-being of human subjects is provided, as well as a method of preparing or optimizing a perfume composition for enhancing the well-being of a human subject, perfume compositions that enhance the well-being, and consumer products containing them.

2 Claims, No Drawings

METHODS OF PREPARING/OPTIMIZING PERFUME COMPOSITIONS

This is an application filed under 35 USC 371 based on PCT/EP2020/062178, filed 1 May 2020, which claims priority to GB 1909221.2, filed 27 Jun. 2019. The present application claims the full priority benefit of all prior applications and incorporates by reference their full disclosures as if set forth herein.

FIELD OF THE INVENTION

The present invention relates to a method of measuring the impact of perfume compositions on the well-being of human subjects, to a method of preparing or optimising perfume compositions that enhance well-being, to perfume compositions that enhance well-being, as well as consumer products containing the perfume compositions.

BACKGROUND OF THE INVENTION

Well-being (or more precisely "subjective well-being") is a complex concept that generally people cannot articulate straightforwardly. Most people would simply equate well-being with the feeling of happiness, or maybe relaxation. A more precise definition of well-being sometimes used in the academic literature refers to well-being as the affective and cognitive assessment by a person of his or her life. In this definition, the so-called "affective" element refers to a person's moods and emotions. A positive affect arises when the moods and emotions experienced are pleasant (e.g. joy, elation, affection, and the like), whereas affect is deemed to be negative when moods and emotions experienced are unpleasant (e.g. guilt, anger, shame, and the like). Psychologically, a person experiences a mood of happiness when the affective balance is such that the positive affect outweighs negative affect.

The other important element of subjective well-being—the so-called "cognitive" element—refers to a person's evaluation of his or her life satisfaction both in global terms (e.g. life as a whole) and in domain terms, such as in terms of satisfaction in personal relationships, the control one has over one's life, one's perceived sense of purpose, and the like.

Well-being is usually measured using self-report methods, typically in the form of questionnaires.

Respondents are asked a series of questions, each relating to a metric relevant to a different subjective state that is considered to have an effect on affective or cognitive elements of well-being. This can include subjective states that have a positive or a negative impact on subjective well-being, e.g. sadness, tiredness, patience, irritation, and the like. For each question, e.g. of the type "are you sad?", respondents are asked to rate the pertinence of each subjective state on a rating scale between polar extremes, e.g. from not very pertinent to highly pertinent. By subjecting a respondent's response data to statistical analysis it is possible to quantify well-being. In this way, many indices have been developed to measure well-being and related concepts. However, knowing which questions to ask can significantly affect the reliability of such measurement techniques.

Reliable means of measuring or rating subjective well-being are highly desirable owing to the economic, political and sociological significance attached to the well-being parameter since the late $20^{th}$ century. Well-being, too, has assumed increased importance more recently as a design parameter in the development and commercialization of consumer products, such as laundry care, household care and personal care products. Manufacturers of these products recognize that modern consumers seek an emotional experience from the products they purchase, and they are particularly interested in brands to which they feel personally connected and which offer them a sense of health and well-being.

Perfumery has been widely employed by consumer product companies in order to impart to their products pleasant, well-liked odours that promote consumer liking and which influence purchasing decisions for this reason.

However, in an increasingly competitive marketplace, mere liking is often not sufficient to differentiate one brand over its competitors. Accordingly, in the market execution of their products, consumer product companies frequently refer to wide-ranging product benefits, typically communicated through diverse advertising campaigns, as well as on the packaging and labelling of their products, which together form an important part of their branding strategy. New differentiating effects are constantly sought, and perfumery has often been employed as a means to achieve those effects. For example, perfumery has been employed to create real or perceived functional effects that may relate to cosmetic effects, hygiene effects, malodour-counteracting effects, and the like.

In addition to its functional effects, odour is known to elicit emotional responses in human subjects. The temporary beneficial psychological effects of odour on human emotions have been studied extensively in the academic literature. For example, the effects of odour on the affective (i.e. emotional) experience of human subjects have been studied by C. Chrea et al. (2009), "Mapping the semantic space for the subjective experience of emotional responses to odours", Chemical Senses, 34 (2009) 49-62 and S. Delplanque et al. "How to map the affective semantic space of Scents", Cognition & Emotion 26(5) (2012) 885-898. In particular, these papers describe a verbal measurement method in the form of a questionnaire, wherein the measurement terms are selected such that it is possible to differentiate the various moods and emotions evoked by odours emanating from perfumed and flavoured products. However, in these papers, the cognitive aspect of well-being is under-estimated and limited to memory aspects associated with the olfactory function.

The patent literature also describes perfume compositions for use in consumer products that are specifically designed to create pleasant mood states (see for example WO 2008/050086 A1) and quality of sleep (see for example WO 2016/146673 A1). However, all of these prior art references touch on only distinct emotional aspects of well-being (e.g. happiness or quality of sleep), without actually addressing both affective and cognitive aspects of well-being as a holistic concept.

Thus, there remains a need to provide a method of measuring the effect of perfume compositions on the subjective well-being of human subjects, as well as a method of preparing and optimizing perfume compositions that enhance the well-being of human subjects.

SUMMARY OF THE INVENTION

In a first aspect, the present invention provides a method of assessing an impact of a test perfume composition on the well-being of human subjects, the method comprising the steps of:
  a) Having one or more human subject(s) assess their well-being in the absence of the test perfume composition by scoring a plurality of well-being attributes;

i) wherein the well-being attributes include "not anxious", "not sad", "not restless", "not frustrated", "not stressed", "happy", "optimistic", "excited", "satisfied", "motivated", "invigorated", "interested", "not bored", "not fatigued", "mentally alert", "calm", "relaxed", and "patient"; and ii) wherein each well-being attribute has a weight;

b) Calculating a base well-being score in the absence of the test perfume composition by multiplying the score of each well-being attribute by the corresponding weight to form a product and summing these products over all well-being attributes;

c) Repeating steps a) and b) in the presence of a test perfume composition in order to determine a well-being score with the test perfume composition; and d) Determining the impact of the test perfume composition on the well-being by subtracting the base well-being score from the well-being score with the test perfume composition.

In a second aspect, the present invention provides a method of preparing or optimizing a perfume composition for enhancing the well-being of a human subject, the method comprising the steps of:

a-d) Assessing the impact of one or more perfume composition(s) on the well-being of human subjects according to the method described above; and e) Selecting a perfume composition with a positive impact on the well-being.

In a third aspect, the present invention provides a perfume composition prepared or optimized according to the method defined above, comprising perfume ingredients from at least three groups, each group each having a different odour attribute, wherein the odour attributes of the groups are selected from the group consisting of "citrus-mandarin", "citrus-orange", "floral-orange flower", "animalic-fecal", "floral-medicinal", "fruity-candied fruit", "spicy-cinnamon", "sweet-tonka", "citrus-lime" and "spicy-clove"; preferably from the group consisting of "citrus-mandarin", "citrus-orange", "floral-orange flower", "animalic-fecal", "floral-medicinal" and "fruity-candied fruit".

In a fourth aspect, the invention provides a consumer product comprising the perfume composition of the present invention and a suitable base.

In a fifth aspect, the invention provides the use of a perfume composition according to the present invention to enhance the well-being of human subjects.

DETAILED DESCRIPTION OF THE INVENTION

In addressing the deficiencies of the prior art, the applicant has carried out extensive studies into the relationship between perfume compositions and the well-being of human subjects, employing measurements of experimental psychology, consumer testing, and statistical analysis.

More particularly, the applicant provides means for reliably assessing the impact of a perfume composition on well-being by means of a questionnaire that breaks down the concept of well-being into key attributes that have an effect on affective or cognitive elements of well-being. The key attributes are weighted in a manner that reflects the relative importance of each attribute to the holistic concept of well-being.

The method of the present invention is particularly sensitive and is able to detect the perception of difficult to detect perfume performance in relation to well-being, which might otherwise be hidden below the noise of liking or perfume intensity if the perfumes were tested using standard consumer testing techniques. In this way, the methods of the present invention offer a useful creation tool to enable creators of perfume compositions to reduce the number of design iterations needed to arrive at a desirable perfume composition.

A well-being metric was defined by applying experimental psychology and unsupervised clustering of verbal attributes of well-being in order to identify the most relevant dimensions to assess well-being. The well-being attributes take into account various aspects of well-being, such as affective, eudaimonic, social, and physical aspects. These aspects may have both affective (emotional) and cognitive (rational) components.

Typical verbal well-being attributes include, for example, "active", "adventurous", "angry", "anxious", "ashamed", "bored", "calm", "cautious", "clear-headed", "comfortable", "confident", "content", "daring", "depressed", "disgusted", "invigorated", "enthusiastic", "excited", "fearful", "frustrated", "happy", "healthy", "impulsive", "in control of your situation", "insecure", "interested", "irritated", "isolated", "joyful", "lonely", "loved", "mentally alert", "motivated", "nervous", "optimistic", "patient", "relaxed", "rested", "restless", "sad", "safe", "satisfied", "self-conscious", "self-esteem", "sociable if in a social environment", "stressed", "supported", "surprised", "threatened", "tired", "uneasy", "vulnerable", "well-being", "worthy" or "worried".

In the course of the studies, 18 verbal attributes were found particularly responsive to change of well-being perception associated with the occurrence of a perfume composition and with changes of perfume quality. These attributes are therefore particularly relevant for investigating how perfumes may influence the well-being of a human subject. These attributes are: "not anxious", "not bored", "calm", "excited", "not fatigued", "not frustrated", "happy", "interested", "invigorated", "mentally alert", "motivated", "optimistic", "patient", "relaxed", "restless", "not sad", "satisfied", and "not stressed". These 18 well-being attributes are referred to as WB-18 attributes hereinafter.

Surprisingly, well-being attributes associated with social aspects, such as "ashamed", "isolated", "lonely", "loved", "sociable if in a social environment", "supported", and "worthy", were found irrelevant or not applicable in the context of perfume compositions. Hence, the WB-18 attributes account principally for both affective (emotional) and cognitive (rational) aspects of the lone individual.

The weighting of the well-being attributes was determined as follows:

a) Having one or more human subject(s) assess their well-being in the absence of a test perfume composition by providing a well-being score for each of the WB-18 attributes;

b) Applying a factor analysis, in particular a principal component analysis, on the well-being scores obtained in step a), in order to determine the impact of each well-being attribute on the overall well-being, resulting in M well-being factors;

i) wherein each of the well-being factors has a variance expressed as a percentage of the sum of the variances of all well-being factors;

ii) wherein each of the well-being factors comprises a finite number of well-being attributes, having a loading, expressed as a percentage of the sum of the loadings; and iii) wherein none of the well-being attributes appears in more than one well-being factor; and c) Calculating the well-being score in the absence of the test perfume according to Equation 1:

$$0 = \Sigma_i = \Sigma\Sigma \quad \text{(Equation 1)}.$$

The principal component analysis revealed that:

the well-being attributes "not anxious", "not sad", "not restless", "not frustrated", "not stressed" are associated with a first well-being factor having a variance;

the well-being attributes "happy", "optimistic", "excited", "satisfied", variance "motivated", "invigorated" are associated with a second well-being factor having a variance;

the well-being attributes "interested" and "not bored" are associated with a third well-being factor having a variance the well-being attributes "not fatigued" and "mentally alert" are associated with a fourth well-being factor having a variance the well-being attributes "calm", "relaxed", and "patient" are associated with a fifth well-being factor having a variance the variance is 48% of the sum of the variances of all well-being factors;

the variance is 24% of the sum of the variances of all well-being factors;

the variance is 12% of the sum of the variances of all well-being factors;

the variance is 9% of the sum of the variances of all well-being factors; and the variance is 7% of the sum of the variances of all well-being factors.

It was further found that, within the first well-being factor, the loading of the well-being attribute "not anxious" is 22.2%, the loading of the well-being attribute "not sad" is 21.5%, the loading of the well-being attribute "not restless" is 20.5%, the loading of the well-being attribute "not frustrated" is 20.1%, and the loading of the well-being attribute "not stressed" is 15.7%;

within the second well-being factor, the loading of the well-being attribute "happy" is 19.6%, the loading of the well-being attribute "optimistic" is 19.2%, the loading of the well-being attribute "excited" is 17.2%, the loading of the well-being attribute "satisfied" is 16.3%, the loading of the well-being attribute "motivated" is 13.9%, and the loading of the well-being attribute "invigorated" is 13.8%;

within the third well-being factor, the loading of the well-being attribute "interested" is 51.0%, and the loading of the well-being attribute "not bored" is 49.0%;

within the fourth well-being factor, the loading of the well-being attribute "not fatigued" is 51.0%, and the loading of the well-being attribute "mentally alert" is 49.0%; and within the fifth well-being factor, the loading of the well-being attribute "calm" is 38.0%, the loading of the well-being attribute "relaxed" is 32.0%, and the loading of the well-being attribute "patient" is 30.0%.

Therefore, in an embodiment of the invention, each well-being attribute has a weight according to the following table:

| well-being attribute | weight |
| --- | --- |
| "not anxious" | 10.65% |
| "not sad" | 10.32% |
| "not restless" | 9.84% |
| "not frustrated" | 9.65% |
| "not stressed" | 7.54% |
| "happy" | 4.70% |
| "optimistic" | 4.61% |
| "excited" | 4.13% |
| "satisfied" | 3.91% |
| "motivated" | 3.34% |
| "invigorated" | 3.31% |
| "interested" | 6.12% |
| "not bored" | 5.88% |
| "not fatigued" | 4.59% |
| "mentally alert" | 4.41% |
| "calm" | 2.66% |
| "relaxed" | 2.24% |
| "patient" | 2.10% |

Preferably, perfume compositions that are not liked by panellists are removed from the list of test perfume compositions to be assessed, as these perfume compositions are unlikely to produce a positive impact on well-being. The degree of liking of the remaining test perfume compositions may still vary according to a pre-defined scale. For example, a vocabulary may be used to define liking, such as "I like this perfume a little", "this perfume is nice" or "I love this perfume". Preferably, the intensity of liking may be expressed by moving a slider button over a continuous range of liking, for example from 1 (I dislike it extremely) to 9 (I like it extremely). The slider may be a physical device or virtual, for example on a digital touch screen.

Similarly, sliders may be used advantageously for scoring the well-being attributes mentioned hereinabove. In this case, the continuous scale underlying the motion of the slider preferably goes from a very negative score to a very positive score. Preferably, the bias induced by variable perfume composition intensity is removed by diluting the powerful perfume compositions, such that all test perfume compositions have nearly the same intensity or strength.

Hence, in an embodiment of the present invention, the strength of the test perfume composition is also assessed by the human subject(s), even if care has been taken to equalize the strength of the test perfume compositions.

By performing a well-being assessment on a plurality of generally well-liked perfume compositions at equal strength, it was surprisingly found that the variance of the impact on the well-being was neither correlated with the variance of perfume liking, nor with the variance of the perfume strength as perceived by individual human subjects. This is shown in Example 3. Thus, a positive impact on well-being is independent from liking of the perfume composition. This is a crucial result, which could not be anticipated by the person skilled in the art. An immediate advantage of this is that it makes possible to elucidate hidden functionalities in consumer studies which would otherwise be overlooked.

In an embodiment, the method of the present invention further comprises the steps of:

f) Comparing the perfume ingredients present in those perfume compositions having a positive impact on the well-being;

g) Identifying odour attributes common to those perfume compositions; and h) Creating a new perfume composition with an increased proportion of perfume ingredients with the odour attributes identified in step g).

Perfume compositions and individual perfume ingredients may be characterized by their odour attributes. Although perfume creation is part science and part artistry, and there is no absolute prescribed definition for odour attributes of perfume compositions and perfume ingredients, nevertheless trained perfumers, realizing that there will be margin for some subjectivity, will be able to assign perfume compositions and ingredients to a general odour descriptor and an odour family.

Odour families provide a general description of an odour space, and their number is usually limited. Hence, most of the ingredients used in perfumery and particularly useful in the context of the present invention may be described by a small set of odour families selected from the group consisting of "aldehyde", "amber", "animalic", "aromatic/herbal", "citrus", "floral", "fruity", "green", "musk", "spicy", "sweet", "watery", and "woody".

Odour descriptors provide a more accurate description of the odour of a perfume composition or ingredient within a family. They are more abundant and their number and diversity is often unlimited. In the context of the present invention, the number of odour descriptors has been limited to a minimal number of verbal items, consisting of "aldehyde zest", "almond", "amber dry", "ambergris", "anis tarragon", "apple", "armoise", "balsam", "banana", "blackcurrant", "butter", "candied fruit", "caraway seed", "cedar", "cinnamon", "citronella", "clove", "cocoa", "coconut", "coniferous", "cooked sugar", "copaiba", "coriander leaf", "cucumber", "eucalyptus", "fecal", "freesia", "galbanum", "grapefruit", "grass", "heliotrope", "jasmine", "lavender", "leaf", "leather", "lemon", "licorice-fenugreek", "lily of the valley", "lime", "liquor", "lychee", "mandarin", "mango", "medicinal", "melon", "metallic", "milk cream", "molasses", "moss", "mushroom", "musk", "musk tonkin", "nut", "orange", "orange flower", "orris", "passionfruit", "patchouli", "peach", "pear", "peppermint", "pineapple", "raspberry", "rhubarb", "rose", "rosemary", "sandalwood", "sea water", "solar", "strawberry", "terpenic", "thyme", "tonka", "vanilla", "vetiver", "violet", and "wax".

This selection of odour families and odour descriptors allows the skilled perfumer to characterize the odour of all perfume ingredients contained in the perfumer's palette. Nevertheless, for the trained perfumer, reading the contents of this specification as a whole together with their common general knowledge it would not present undue burden to modify part or all of this vocabulary around which there is subjectivity, and such modification would not impact the selection of perfume ingredients useful to positively impact the perception of well-being.

The set of odour families and descriptors may be assimilated to the dimensions of a multidimensional odour space.

The overall odour of a perfume composition may be expressed as the weighted sum of the contribution of the odour attributes of the individual perfume ingredients comprised in the perfume composition. Because of the high dimensionality of the odour, it may be convenient to reduce this high dimensionality by applying statistical methods such as principal component analysis, multiple scaling or self-organized maps. Preferably, principal component analysis (PCA) is used.

The applicant has now discovered that certain odour attributes impact well-being more positively than others and that a classification of the perfume ingredients according to their position in the odour space and impact on the perception of well-being is possible.

In particular, it was found that perfume compositions having odour attributes such as "citrus-mandarin", citrus-orange", "floral-orange flower", "fruity-candied fruit", "floral-medicinal", and "animalic-fecal" have a highly positive impact on well-being, whereas perfumes having odour attributes such as "spicy-cinnamon", "sweet-tonka", "citrus-lime", and "spicy-clove" are less performing. These results may also be considered as surprising for the person skilled in the art, in particular for the evaluator and the perfumer, who would not anticipate that odour attributes like "floral-medicinal" and "animalic-fecal" have a more positive impact on well-being than "spice cinnamon" or "citrus-lime" do.

Therefore, in one embodiment of the present invention, the proportion of one or more perfume ingredient(s) having odour attributes selected from the group consisting of "citrus-mandarin", "citrus-orange", "floral-orange flower", "animalic-fecal", "floral-medicinal", "fruity-candied fruit", "spicy-cinnamon", "sweet-tonka", "citrus-lime" and "spicy-clove" is increased in step h); more preferably of one or more perfume ingredient(s) having odour attributes selected from the group consisting of "citrus-mandarin", "citrus-orange", "floral-orange flower", "animalic-fecal", "floral-medicinal" and "fruity-candied fruit".

Hence, the present invention teaches the skilled perfumer how to formulate perfume compositions in a manner in which they are likely to arrive quickly at a perfume composition that will induce or be associated with an increase of well-being. The effects are sufficiently pronounced that they can be measured reliably and reproducibly. The perfume compositions made according to the teaching disclosed herein can be hedonically pleasant, suitable for a wide range of consumer products, and of sufficient pleasantness/acceptability that they would be appropriate even if they did not possess the added functionality.

The method of the present invention has been found to allow the preparation or optimization of perfume compositions to enhance the well-being of human subjects by:
promoting a reduction in negativity, namely how anxious, sad, restless, frustrated and/or stressed a subject is reporting to feel; and/or
promoting an increase in positivity, namely how happy, optimistic, excited, satisfied, motivated and/or invigorated a subject is reporting to feel; and/or
promoting an increase in interest, namely how more interested and/or less bored a subject is reporting to feel; and/or
promoting a decrease in tiredness, namely how less fatigued and/or more mentally alert a subject is reporting to feel; and/or
promoting an increase in calmness, namely how calm, relaxed and/or patient a subject is reporting to feel.

The invention also provides perfume compositions comprising well-being enhancing perfume ingredients selected by the methods described herein. In particular, the present invention enables the skilled perfumer to:
i) compare perfume ingredients contained in perfume compositions found to have a positive effect on the well-being in human subjects;
ii) identify odour attributes common to these perfume ingredients; and
iii) propose new perfume compositions containing increased quantities of ingredients having odour attributes identified in step b).

The present invention provides perfume compositions for enhancing well-being, comprising perfume ingredients from at least three groups, each group having a different odour attribute, wherein the odour attributes of the groups are selected from the group consisting of "citrus-mandarin", "citrus-orange", "floral-orange flower", "animalic-fecal", "floral-medicinal", "fruity-candied fruit", "spicy-cinnamon", "sweet-tonka", "citrus-lime", and "spicy-clove"; more preferably from the group consisting of "citrus-mandarin", "citrus-orange", "floral-orange flower", "animalic-fecal", "floral-medicinal", and "fruity-candied fruit".

In an embodiment of the invention, the perfume composition comprises one or more perfume ingredients having a "citrus-orange" odour attribute in a concentration of from 0.1 to 25 wt.-%, more particularly of from 0.2 to 15 wt.-%, and still more particularly from 0.25 to 10 wt.-%.

In an embodiment of the invention, the perfume composition comprises one or more perfume ingredients having a "citrus-lime" odour attribute in a concentration of from 0.05 to 5 wt.-%, more particularly of from 0.1 to 3 wt.-%, and still more particularly from 0.12 to 1.5 wt.-%.

In an embodiment of the invention, the perfume composition comprises one or more perfume ingredients having a "citrus-mandarin" odour attribute in a concentration of from 0.05 to 5 wt.-%, more particularly of from 0.1 to 3 wt.-%, and still more particularly from 0.12 to 1.5 wt.-%.

In an embodiment of the invention, the perfume composition comprises one or more perfume ingredients having a "sweet-tonka" odour attribute in a concentration of from 0.05 to 1 wt.-%, more particularly of from 0.07 to 0.9 wt.-%, and still more particularly from 0.1 to 0.75 wt.-%.

In an embodiment of the invention, the perfume composition comprises one or more perfume ingredients having a "fruity-candied fruit" odour attribute in a concentration of from 0.01 to 1 wt.-%, more particularly of from 0.02 to 0.9 wt.-%, and still more particularly from 0.03 to 0.65 wt.-%.

In an embodiment of the invention, the perfume composition comprises one or more perfume ingredients having a "floral-orange flower" odour attribute in a concentration of from 0.01 to 1 wt.-%, more particularly of from 0.025 to 0.75 wt.-%, and still more particularly from 0.03 to 0.5 wt.-%.

In an embodiment of the invention, the perfume composition comprises one or more perfume ingredients having a "floral-orange medicinal" odour attribute in a concentration of from 0.01 to 1.0 wt.-%, more particularly of from 0.02 to 1.0 wt.-%, and still more particularly from 0.035 to 0.5 wt.-%.

In an embodiment of the invention, the perfume composition comprises one or more perfume ingredients having a "spicy-clove" odour attribute in a concentration of from 0.005 to 0.7 wt.-%, more particularly of from 0.01 to 0.5 wt.-%, and still more particularly from 0.02 to 0.25 wt.-%.

In an embodiment of the invention, the perfume composition comprises one or more perfume ingredients having an "animalic-fecal" odour attribute in a concentration of from 0.005 to 0.07 wt.-%, more particularly of from 0.07 to 0.05 wt.-%, and still more particularly from 0.01 to 0.030 wt.-%.

In an embodiment of the invention, the perfume composition comprises one or more perfume ingredients having a "spicy cinnamon" odour attribute in a concentration of from 0.0001 to 0.05 wt.-%, more particularly of from 0.001 to 0.025 wt.-%, and still more particularly from 0.005 to 0.01 wt.-%.

Throughout this application, the weight percentages wt.-% are based on the total weight of the perfume ingredients present in a perfume composition unless otherwise indicated.

Preferably, each of the above groups is present in the above indicated concentrations if present at all.

In an embodiment of the invention, the perfume composition comprises one or more perfume ingredients having a "citrus-orange" odour attribute, selected from the group consisting of ORANGE OILS AND ORANGE RECONSTITUTIONS, such as ORANGE BRAZIL CRUDE OIL, GRAPEFRUIT OIL, ORANGE OIL, ORANGE BITTER OIL, ORANGE BLOOD OIL; ORANGE OIL COLORLESS, ORANGE OIL CONCENTRATED, ORANGE ESSENCE, ORANGE TERPENES, BIGARADE PHASE OIL, TANGELO OIL, natural orange carbonyls and aldehydes, and mixtures thereof.

In an embodiment of the invention, the perfume composition comprises one or more perfume ingredients having a "citrus-lime" odour attribute, selected from the group consisting of CYMENE PARA (4-methyl-1-isopropylbenzene), CEDRAT OIL, CITRATHAL R (1,1-diethoxy-3,7-dimethylocta-2,6-diene), DELTA-3-CARENE (3,7,7-trimethylbicyclo[4.1.0]hept-3-ene), DIPENTENE (1-methyl-4-(prop-1-en-2-yl)cyclohex-1-ene), ELEMI OIL, ELEMI RESINOID, LEMON GREEN PHASE OIL, KIME DIENES, LIME OIL DISTILLED, LIME OIL EXPRESSED, LIME OXIDE, LIME TERPENE RECONSTITUTION, OCIMENE ((E)-3,7-dimethylocta-1,3,6-triene), TERPINENE ALPHA (1-methyl-4-propan-2-ylcyclohexa-1,3-diene), TERPINENE GAMMA (1-methyl-4-propan-2-ylcyclohexa-1,4-diene), TERPINEOL (2-(4-methyl-3-cyclohexen-1-yl)-2-propanol) and TERPINOLENE (1-methyl-4-propan-2-ylidenecyclohexene), and mixtures thereof.

In an embodiment of the invention, the perfume composition comprises one or more perfume ingredients having a "citrus-mandarin" odour attribute, selected from the group consisting of CLEMENTINE OIL, DIMETHYL ANTHRANILATE (methyl 2-methylaminobenzoate), MANDARIN OIL, MADARIN OIL COLORLESS, MANDARIN GREEN OIL, MANDARIN YELLOW OIL, MANDARINE PHASE OIL, TAMARIN OIL, TAMARIN RECONSTITUTIONS, TANGERINE OIL, TANGERINE RECONSTITUTION, TANGERINOL ((E)-6,10-dimethylundeca-5,9-dien-2-yl acetate), and mixtures thereof.

In an embodiment of the invention, the perfume composition comprises one or more perfume ingredients having a "sweet-tonka" odour attribute, selected from the group consisting of BICYCLO NONALACTONE (3,4,4a,5,6,7,8,8a-octahydrochromen-2-one), COUMARIN (chromen-2-one), and TOLYL ALDEHYDE PARA (4-methylbenzaldehyde), COUMARIN RECONSTITUTION, FLOUVE OIL, FLOUVE RECONSTITUTION, HAY OIL, HAY ABSOLUTE, KOUMALACTONE (3,6-dimethyl-3a,4,5,6,7,7a-hexahydro-3H-benzofuran-2-one), MARSHMALLOW ABSOLUTE, MATE ABSOLUTE, MATE RECONSTITUTION, METHYL OCTALACTONE (5-butyl-4-methyloxolan-2-one), TONKAROSE ((E)-dec-9-en-1-yl 3-(2-hydroxyphenyl)acrylate), SESAME ROASTED ABSOLUTE, TOBACCO LEAF ABSOLUTE, TONKA ABSOLUTE, TONKA ABSOLUTE COLORLESS, TONKA BEAN OIL, ACETANISOLE (1-(4-methoxyphenyl)ethanone), ACETOPHENONE EXTRA (1-phenylethanone), ANISIC ALDEHYDE (4-methoxybenzaldehyde), ANISYL ALCOHOL ((4-methoxyphenyl)methanol), AUBEPINE PARA CRESOL (4-methoxybenzaldehyde), DIMETHYL HYDROQUINONE CRYSTALS (1,4-dimethoxybenzene), HELIOTROPINE CRYSTALS (benzo[d][1,3]dioxole-5-carbaldehyde), HYDRATROPIC ALDEHYDE (2-phenylpropanal), METHYL ACETOPHENONE (1-(p-tolyl)ethanone), MIMOSA ABSOLUTE, VERATRYL ALDEHYDE (3,4-dimethoxybenzaldehyde), and mixtures thereof.

In an embodiment of the invention, the perfume composition comprises one or more perfume ingredients having a "fruity-candied fruit" odour attribute, selected from the group consisting of CRISTALON (ethyl 2,6,6-trimethylcyclohexa-1,3-diene-1-carboxylate), GIVESCONE (ethyl 2-ethyl-6,6-dimethylcyclohex-2-ene-1-carboxylate), DAMASCENONE ((E)-1-(2,6,6-trimethylcyclohexa-1,3-dien-1-yl)but-2-en-1-one), DAMASCONE ALPHA ((E)-1-(2,6,6-trimethyl-1-cyclohex-2-enyl)but-2-en-1-one), DAMASCONE BETA ((E)-1-(2,6,6-trimethyl-1-cyclohexenyl)but-2-en-1-one), DAMASCONE DELTA (1-(2,6,6-trimethyl-1-cyclohex-3-enyl)but-2-en-1-one, more particularly (E)-1-(2,6,6-trimethyl-1-cyclohex-3-enyl)but-2-en-1-one), and POMAROSE ((2E,5Z)-5,6,7-trimethylocta-2,5-dien-4-one), and mixtures thereof.

In an embodiment of the invention, the perfume composition comprises one or more perfume ingredients having a "floral-orange flower" odour attribute, selected from the group consisting of ORANGE FLOWER RECONSTITUTIONS, METHYL ANTHRANILATE (methyl 2-aminobenzoate), ORANGER CRYSTALS (1-naphthalen-2-ylethanone), JASMIN SAMBAC OIL, and mixtures thereof.

In an embodiment of the invention, the perfume composition comprises one or more perfume ingredients having a "floral-medicinal" odour attribute, selected from the group consisting of YARA YARA (2-methoxynaphthalene), CRESYL METHYL ETHER PARA (1-methoxy-4-methylbenzene), ETHYL BENZOATE, ETHYL SALICYLATE, METHYL BENZOATE, METHYL SALICYLATE, TUBEREUSE FLOWER RECONSTITUTIONS, and mixtures thereof.

In an embodiment of the invention, the perfume composition comprises one or more perfume ingredients having a "spicy-clove" odour attribute, selected from the group consisting of EUGENYL ACETATE ((2-methoxy-4-prop-2-enylphenyl) acetate), ACETYL ISOEUGENOL (2-methoxy-4-prop-1-en-2-ylphenol acetate), crude, colourless and rectified CLOVE LEAF OIL, DIHYDRO EUGENOL (2-methoxy-4-propylphenol), EUGENOL (2-methoxy-4-prop-2-enylphenol), and ISOEUGENOL (2-methoxy-4-prop-1-en-2-ylphenol), and mixtures thereof.

In an embodiment of the invention, the perfume composition comprises one or more perfume ingredients having an "animalic-fecal" odour attribute, selected from the group consisting of INDOLE and INDOLENE (8,8-bis(1H-indol-3-yl)-2,6-dimethyloctan-2-ol), INDOFLOR (4,4a,5,9b-tetrahydroindeno[1,2-d][1,3]dioxine), and mixtures thereof.

In an embodiment of the invention, the perfume composition comprises one or more perfume ingredients having a "spicy cinnamon" odour attribute, selected from the group consisting of CINNAMIC ALDEHYDE (3-phenylprop-2-enal), CINNAMALVA ((E)-3-phenylprop-2-enenitrile), CINNAMON BARK OIL; METHYL CINNAMIC ALDEHYDE ((Z)-2-methyl-3-phenylacrylaldehyde) and mixtures thereof.

In an embodiment of the invention, the perfume composition comprises INDOLE in combination with at least five, more particularly at least six perfume ingredients selected from the group consisting of CITRONELLOL (3,7-dimethyloct-6-en-1-ol), DECALACTONE GAMMA (5-hexyloxolan-2-one), GARDENOL (1-phenylethyl acetate), HEXENOL-3-CIS ((Z)-hex-3-en-1-ol), IONONE BETA (4-(2,6,6-trimethylcyclohexen-1-yl)but-3-en-2-one), LINALOOL (3,7-dimethylocta-1,6-dien-3-ol), LINALYL ACETATE (3,7-dimethylocta-1,6-dien-3-ol acetate) and PEACH PURE (5-heptyloxolan-2-one); or at least five, more particularly at least six perfume ingredients selected from the group consisting of CITRONELLOL (5-heptyloxolan-2-one), ETHYLENE BRASSYLATE (1,4-dioxacycloheptadecane-5,17-dione), BENZYL ACETATE, HEDIONE (methyl 3-oxo-2-pentylcyclopentaneacetate), LINALOOL (3,7-dimethylocta-1,6-dien-3-ol), ISO E SUPER (1-(2,3,8,8-tetramethyl-1,3,4,5,6,7-hexahydronaphthalen-2-yl)ethanone), PHENYL ETHYL ALCOHOL, ETHYL VANILLIN, and VANILLIN.

In an embodiment of the invention the perfume composition comprises DAMASCENONE in combination with at least five, more particularly at least six perfume ingredients selected from the group consisting of CITRONELLOL (3,7-dimethyloct-6-en-1-ol), GARDENOL (1-phenylethyl acetate), HEXENYL-3-CIS ACETATE ((Z)-hex-3-en-1-ol), IONONE BETA (4-(2,6,6-trimethylcyclohexen-1-yl)but-3-en-2-one), LINALOOL (3,7-dimethylocta-1,6-dien-3-ol), LINALYL ACETATE (3,7-dimethylocta-1,6-dien-3-ol acetate), and PEACH PURE (5-heptyloxolan-2-one).

In the context of the present invention, the term "perfume ingredient" refers to an ingredient that has the function of providing a noticeable and identifiable odour to the perfume composition. Perfume ingredients include highly performing ingredients intended for providing an intense olfactive impression, as well as less performing ingredients intended for providing a subtle olfactive impression.

Certain perfume ingredients referred to herein are denoted as "reconstitutions". A reconstitution is a mixture of perfume ingredients, the purpose of which is to mimic a specific odour, for example that of a "blood orange" or a "green apple".

Where trivial names are used to describe useful perfume ingredients herein, the skilled perfumer will understand that these are commonly used names in the art of perfumery. However, the skilled perfumer would also understand that these ingredients may also be known by other trivial synonyms, by CAS registry numbers, or by more formal nomenclature, such as IUPAC nomenclature. Furthermore, the skilled perfumer would be familiar with these other trivial synonyms, as well as with more formal nomenclature, or at the least, would be aware of standard reference works, such as The Good Scents Company website, which contains a comprehensive list of trivial names, registry numbers and more formal nomenclature for the perfume ingredients contained in the perfumers' palette.

The perfume compositions of the present invention may be entirely comprised of perfume ingredients referred to hereinabove. However, in addition to the perfume ingredients referred to hereinabove, the perfume compositions of the present invention may contain other perfume ingredients. A comprehensive list of other suitable perfume ingredients may be found in the perfumery literature, for example "Perfume & Flavor Chemicals", S. Arctander (Allured Publishing, 1994), as well as later editions of this work, which perfume ingredients contained therein are herein incorporated by reference.

Perfume compositions of the present invention may further contain substantially odourless ingredients. In the context of the present invention, "substantially odourless" means that the ingredient has no odour or that its odour is weak and often barely perceptible. These substantially odourless ingredients include excipients conventionally used in conjunction with perfume ingredients in perfume compositions, for example carrier materials, and other auxiliary agents commonly used in the art, e.g. solvents, such as dipropylene glycol (DPG), isopropyl myristate (IPM), benzyl benzoate (BB), propylene glycol (PG) and triethyl citrate (TEC); mineral oils and vegetable oils; and antioxidants. As such, these substantially odourless ingredients are not considered to be perfume ingredients in the context of the present invention. In particular, solvents are not taken into account when calculating the weight percentages.

The perfume compositions of the present invention may be presented in the form of free-oil, or they may be encapsulated. Several encapsulating media are known in the art for encapsulating perfume compositions. Particular encapsulating media include microcapsules formed of aminoplast resins, such as melamine-formaldehyde resins, polyurea, polyamide, as well as copolymers of acrylic acid, methacrylic acid and their esters. Alternatively, the encapsulating media may be formed of natural or modified natural polymers, such as polysaccharides or proteins.

The perfume compositions of the present invention may be used to impart desirable odour impressions on all manner of consumer products, such as for instance hydro-alcoholic perfumes, deodorants, antiperspirants, skin care products, hair care products, laundry care products, home care products or air fresheners.

More particularly, the perfume compositions of the present invention may be employed in laundry care applications, personal care products for treating the hair and/or skin of human subjects, oral care products, and air care products.

Consumer products comprise formulated mixtures of various functional ingredients, such as surfactants, emulsifiers, polymers, fillers and solvents. These formulated mixtures are usually referred to as "bases".

Particular consumer products include, but are not limited to consumer products intended for application to the body (i.e. skin or hair), to hard surfaces (e.g. kitchen and bathroom worktops, ceramic surfaces), to fabrics, and for air care benefits (e.g. air-fresheners). Such products can take a variety of forms, including, but not limited, to powders, bars, sticks, tablets, creams, mousses, gels, liquids, sprays and sheets. The proportion of perfume composition contained in such products may lie in a range from 0.05% (as for example in a low odour skin cream) to 100 wt.-% (as for example in an air freshener) based on the total weight of the consumer product. The means of incorporating a perfume composition into a consumer product is known. Existing techniques may be used for incorporating the perfume composition directly into a product, or the perfume composition may be absorbed on a carrier material and then admixed to the product.

The invention thus also provides a consumer product comprising the perfume composition of the present invention.

In an embodiment of the present invention, the consumer product is a laundry care product. Laundry care products include powder and liquid detergents and fabric softeners, stain removers and pre-wash treatments, conditioners and softeners (including standard and concentrated conditioners, softeners and dryer sheets), laundry aids (including stain removers, ironing aids, whiteners and colour care products and other ancillary fabric care products), laundry detergents (including machine wash liquid detergents, other machine wash detergents—including powders, capsules and tablets—and hand wash detergents—powders, flakes and cakes/bars), sheet sprays, clothing sprays, laundry perfumes, dryer sachets, perfumed sachets, dryer sheets, laundry soap, laundry detergents, detergent for delicate textiles, ironing sprays, starch, perfume sheets, pillow mists, drawer liner sheets, cedar closet sprays, linen waters, and refills and combinations thereof.

In an embodiment of the invention, the consumer product is a personal care product. Personal care products include soaps, shower gels, body creams, body lotions, body mists, perfumery, cosmetics, floating bath oils, after shaves, creams, lotions, deodorants (including stick deodorants), pre-electric shave lotions, after-shave lotions, antiperspirants, shampoos, conditioners, rinses, skin care products, eye makeups, body shampoos, protective skin formulations, lipsticks, lip glosses, after-bath splashes, pre-sun and sun products (including sunscreens). Virtually any chemical product which comes into contact with the hair or skin and which may include effective amounts, concentrations or proportions of one or more of the perfume compositions of the present invention may be considered a personal care product according to the present invention.

In an embodiment of the invention, the consumer product is an oral care product. Oral care products include toothpastes, dental creams, gels or tooth powders, odontic, mouth washes (including plaque removing liquids), pre- or post-brushing rinse formulations, chewing gums, lozenges, and candy.

In an embodiment of the present invention, the consumer product is an air care product. Air care products include candles and air-freshener devices, such as liquid electrical air-freshener devices, aerosol sprays, pump action sprays, perfumed candles, membrane permeation devices, liquid wick devices, oil based gel perfumes, and aqueous gels.

In an embodiment of the present invention, the consumer product is a home care product. Home care products can be used particularly for cleaning, rinsing, care or treatment of industrial, domestic or communal hard surfaces, as well as textile article surfaces; they are targeted at conferring on the surfaces treated therewith benefits such as water repellency, soil release, stain resistance, anti-fogging, surface repair, anti-wrinkling, shine, lubrication and/or at improving the residuality, impact and/or efficacy of active materials comprised in said home care product. Hence, home care compositions according to the invention include surface cleaning compositions (for example glass, floor, counter, bath, toilet bowl, sink, appliance and furniture cleaning compositions), disinfectants (for example spray and solid air disinfectants, including gels, and spray, solid, liquid and paste surface disinfectants), waxes and other surface protecting and/or polishing compositions, and rug shampoos.

The methods of the present invention may be facilitated by computer means.

The computer means may comprise suitable hardware and software components commonly known and used in the art.

The computer means may comprise a database of perfume ingredients or perfume compositions in computer readable form. For each perfume ingredient or perfume composition, the database may contain at least one defining parameter, property or function of that ingredient or composition. In particular, for each perfume ingredient or composition, there may be assigned a well-being score defined according to the methods described above.

The computer means may comprise data-processing means configured and operable to allow a formulator to select perfume ingredients from the database, and to calculate a well-being score for a perfume composition containing the selected perfume ingredients.

Hereinafter, the present invention will be described in further detail with reference to examples. It is to be understood, however, that these examples are for illustrative purposes only and are not to be construed to limit the scope of the present invention.

Example 1: Development of the Well-being Metric (WB-18)

A. Identification of Well-being Attributes

In a preliminary study, a broad selection of verbal well-being attributes was considered and those which were shown to be sensitive to the action of odour were retained. The most relevant of these attributes were those which showed significant differences between control, malodours and/or perfume conditions and, importantly, between pleasant perfumes. This led to a subset of 18 attributes, which showed the highest sensitivity to perfume, according to principal component analysis. The thus identified WB-18 attributes are listed in Table 1 below.

Each item was assessed by panellists moving a virtual slider on a touch screen. 138 panellists across four different studies completed the assessment.

Panellists first completed two baseline measures of the WB-18 attributes in the absence of and before exposure to a test perfume composition, with the second baseline measure being completed immediately after the first one. Factor analysis (see above) was applied to the averaged baseline data to determine five well-being factors and the related variances, as well as the loadings for each well-being attribute within the five well-being factors (see Table 1). Factor loadings are based on a principal axis factoring with oblimin rotation because of the possible correlations between some of the well-being attributes.

TABLE 1

Well-being attributes, factors and factor loadings obtained from principal component analysis

| Attribute | Factor 1 (variance = 0.48) | Factor 2 (variance = 0.24) | Factor 3 (variance = 0.12) | Factor 4 (variance = 0.09) | Factor 5 (variance = 0.07) |
| --- | --- | --- | --- | --- | --- |
| Not anxious | 0.222 | | | | |
| Not sad | 0.215 | | | | |
| Not restless | 0.205 | | | | |
| Not frustrated | 0.201 | | | | |
| Not stressed | 0.157 | | | | |
| Happy | | 0.196 | | | |
| Optimistic | | 0.192 | | | |
| Excited | | 0.172 | | | |
| Satisfied | | 0.163 | | | |
| Motivated | | 0.139 | | | |
| Invigorated | | 0.138 | | | |
| Interested | | | 0.510 | | |
| Not bored | | | 0.490 | | |
| Not fatigued | | | | 0.510 | |
| Mentally alert | | | | 0.490 | |
| Calm | | | | | 0.380 |
| Relaxed | | | | | 0.320 |
| Patient | | | | | 0.300 |

Based on the above analysis, the weighting for each well-being attribute was determined as shown in Table 2:

TABLE 2

Weighting of the well-being attributes

| well-being attribute | weight |
| --- | --- |
| "not anxious" | 10.65% |
| "not sad" | 10.32% |
| "not restless" | 9.84% |
| "not frustrated" | 9.65% |
| "not stressed" | 7.54% |
| "happy" | 4.70% |
| "optimistic" | 4.61% |
| "excited" | 4.13% |
| "satisfied" | 3.91% |
| "motivated" | 3.34% |
| "invigorated" | 3.31% |
| "interested" | 6.12% |
| "not bored" | 5.88% |
| "not fatigued" | 4.59% |
| "mentally alert" | 4.41% |
| "calm" | 2.66% |
| "relaxed" | 2.24% |
| "patient" | 2.10% |

B. Methodology Protocol for Well-being Study 690 subjects between the ages of 21 and 53 (283 male and 407 female) were recruited for this study. Subjects were native English speakers with normal or corrected vision, and recruited from the general public in the UK. All subjects indicated that they had no known deficits in their sense of smell, olfactory sensitivities or neurological diseases. Test perfume compositions were applied onto Sorbarods consisting of an extruded polyester fibre rod, ex Porex. Each participant received four different test perfume compositions, with instructions to smell and score online one sample per day at approximately the same time of their choosing.

Each day, the participants first scored the WB-18 attributes in the absence of a test perfume composition.

Participants were then instructed to take three sniffs from the Sorbarod to which the test perfume composition had been applied, with additional instructions to take another three sniffs after completing 50% of the test.

The well-being attributes were randomised for each participant for each assessment.

After completing the scoring of all WB-18 attributes of the fourth sample, on the fourth day, participants were asked to provide a series of ratings of the test perfume compositions they had smelt over the four days. The order of the samples was randomised again with instructions to sniff each sample individually and complete the ratings for each sample before smelling the next. For each test perfume composition, participants provided a liking rating on a scale of 1 (I dislike it extremely) to 9 (I like it extremely).

| I dislike it extremely | I dislike it very much | I dislike it moderately | I dislike it slightly | I neither like nor dislike it | I like it slightly | I like it moderately | I like it very much | I like it extremely |
|---|---|---|---|---|---|---|---|---|
| 1 | 2 | 3 | 4 | 5 | 6 | 7 | 8 | 9 |

In addition, participants provided a strength rating on a scale of 1 (extremely weak) to 9 (extremely strong).

| Extremely weak | Very weak | Quite weak | Slightly weak | Neither weak nor strong | Slightly strong | Quite strong | Very strong | Extremely strong |
|---|---|---|---|---|---|---|---|---|
| 1 | 2 | 3 | 4 | 5 | 6 | 7 | 8 | 9 |

C. Measurement of the Impact of the Test Perfume Composition on Well-being 18 test perfume compositions with presumed equal liking scores were selected by a panel of two experts The strength (intensity) of these 18 test perfume compositions was estimated by a panel of 15 trained panellists and a dilution factor was defined depending on the difference of strength between all test perfume compositions and the test perfume composition which was the least intensive in the set. The dilution factor was used to equalize the odour intensity of the test perfume compositions.

The thus prepared 18 test perfume compositions were applied to Sorbarods and submitted to the participants of the study for well-being assessment according to the method described in Section B.

The participants assessed the WB-18 attributes providing a first individual well-being score (=base) well-being score for each well-being attribute in the absence of a test perfume composition (w/o) and a second individual well-being score in the presence of each test perfume composition (w). The corresponding well-being scores were calculated by multiplying the individual score of each well-being attribute by the weighting as determined in Section A (see Table 2) and summing up the individual scores.

Finally, the well-being enhancement score was calculated by subtracting the base well-being score (i.e. the sum of the first individual well-being scores multiplied by their weightings) from the well-being score with the test perfume composition (i.e. the sum of the second individual well-being scores multiplied by their weightings). Average results over all participants are shown in Table 3.

TABLE 3

Averaged well-being scores before and after having smelt the test perfume compositions, and well-being enhancement in percent

|  | Before | After | Well-being enhancement score |
|---|---|---|---|
| Perfume 6 | 7.13 | 7.58 | 6.3% |
| Perfume 11 | 6.81 | 7.25 | 6.5% |
| Perfume 16 | 7.07 | 7.51 | 6.2% |
| Perfume 8 | 6.85 | 7.25 | 5.8% |
| Perfume 2 | 6.78 | 7.16 | 5.6% |
| Perfume 10 | 6.92 | 7.24 | 4.6% |
| Perfume 12 | 6.89 | 7.20 | 4.5% |
| Perfume 5 | 6.91 | 7.22 | 4.5% |
| Perfume 13 | 6.74 | 7.04 | 4.5% |
| Perfume 14 | 7.08 | 7.36 | 4.0% |
| Perfume 3 | 6.67 | 6.94 | 4.0% |
| Perfume 15 | 6.78 | 7.04 | 3.8% |

TABLE 3-continued

Averaged well-being scores before and after having smelt the test perfume compositions, and well-being enhancement in percent

|  | Before | After | Well-being enhancement score |
|---|---|---|---|
| Perfume 7 | 6.97 | 7.22 | 3.6% |
| Perfume 9 | 6.82 | 7.06 | 3.5% |
| Perfume 17 | 6.70 | 6.94 | 3.6% |
| Perfume 1 | 6.82 | 7.05 | 3.4% |
| Perfume 4 | 7.09 | 7.32 | 3.2% |
| Perfume 18 | 6.81 | 6.82 | 0.1% |

Example 2: Identification of Odour Attributes Related to Positive Impact on Well-being For each of the 18 test perfume compositions assessed in Section C. of Example 1, the odour attributes of the perfume ingredients contained were determined. A Principal Component Analysis (PCA) was performed in order to provide maximal differentiation of the 18 perfume compositions in a two-dimensional projection of the odour space. Each test perfume composition was tagged by its well-being enhancement rating (last column in Table 3).

It was found that a total of ten odour attributes are correlated to the enhancement of well-being, with six of them being related to a strong well-being enhancement:

Odour attributes with strong positive impact on well-being:—"floral-orange flower"

"floral-medicinal"

"animalic-fecal"

"citrus-orange"

"citrus-mandarin"

"fruity-candied fruit"

Odour attributes with positive impact on well-being:—"spicy-cinnamon"

"sweet-tonka"

"citrus-lime"

"spicy-clove"

TABLE 4

Composition based on odour descriptions of test perfume compositions 1 to 9

| | Ingredients | Test Perfume Compositions | | | | | | | | |
|---|---|---|---|---|---|---|---|---|---|---|
| | | 1 | 2 | 3 | 4 | 5 | 6 | 7 | 8 | 9 |
| 1 | Aldehydic-Aldehyde Zest | 0.05 | 1.57 | 0.02 | 0.09 | 1.60 | 0.06 | 1.04 | 0.00 | 0.00 |
| 2 | Aldehydic-Coriander Leaf | 0.00 | 0.00 | 0.00 | 0.00 | 0.00 | 0.00 | 0.06 | 0.00 | 0.00 |
| 3 | Aldehydic-Mandarin | 0.00 | 0.00 | 0.00 | 0.00 | 0.00 | 0.00 | 0.10 | 0.00 | 0.00 |
| 4 | Amber-Amber Dry | 0.00 | 0.00 | 0.00 | 0.00 | 0.00 | 0.00 | 0.00 | 0.00 | 0.00 |
| 5 | Amber-Ambergris | 0.13 | 0.01 | 0.04 | 0.06 | 0.29 | 0.00 | 0.00 | 0.00 | 0.00 |
| 6 | Animalic-Fecal | 0.00 | 0.00 | 0.00 | 0.00 | 0.04 | 0.02 | 0.00 | 0.00 | 0.00 |
| 7 | Animalic-Leather | 1.26 | 0.02 | 0.00 | 0.00 | 0.00 | 0.00 | 0.00 | 0.00 | 0.00 |
| 8 | Aromatic herbal-Anis Tarragon | 0.00 | 0.17 | 0.15 | 0.15 | 0.07 | 0.00 | 0.00 | 0.00 | 0.00 |
| 9 | Aromatic herbal-Armoise | 0.05 | 0.12 | 0.00 | 0.00 | 0.15 | 0.00 | 0.00 | 0.00 | 0.00 |
| 10 | Aromatic herbal-Caraway Seed | 0.00 | 0.93 | 0.07 | 0.07 | 0.00 | 0.00 | 5.20 | 0.00 | 0.00 |
| 11 | Aromatic herbal-Coniferous | 0.00 | 15.00 | 3.32 | 1.50 | 0.00 | 0.00 | 0.00 | 0.00 | 0.00 |
| 12 | Aromatic herbal-Eucalyptus | 0.00 | 8.69 | 2.21 | 0.30 | 0.00 | 0.00 | 3.12 | 0.00 | 0.00 |
| 13 | Aromatic herbal-Lavender | 10.89 | 23.25 | 18.79 | 8.99 | 13.06 | 2.49 | 0.00 | 0.00 | 11.51 |
| 14 | Aromatic herbal-Peppermint | 0.00 | 20.25 | 0.37 | 0.07 | 0.00 | 0.00 | 14.55 | 0.00 | 0.00 |
| 15 | Aromatic herbal-Thyme | 0.05 | 0.35 | 0.00 | 0.00 | 0.00 | 0.00 | 4.16 | 0.00 | 0.00 |
| 16 | Citrus-Grapefruit | 3.79 | 0.00 | 0.00 | 0.00 | 0.00 | 0.62 | 0.00 | 0.00 | 0.00 |
| 17 | Citrus-Lemon | 11.38 | 0.23 | 0.00 | 0.30 | 1.45 | 3.61 | 31.1 | 0.00 | 0.00 |
| 18 | Citrus-Lime | 0.00 | 0.00 | 0.00 | 0.00 | 0.00 | 0.00 | 0.00 | 0.00 | 0.00 |
| 19 | Citrus-Lime | 1.26 | 0.00 | 0.00 | 0.00 | 0.00 | 0.00 | 0.00 | 0.00 | 0.00 |
| 20 | Citrus-Lime | 0.00 | 0.00 | 0.00 | 0.00 | 0.00 | 0.00 | 0.00 | 0.00 | 0.00 |
| 21 | Citrus-Lime | 0.00 | 0.00 | 0.00 | 0.00 | 0.00 | 0.00 | 0.00 | 0.00 | 0.00 |
| 22 | Citrus-Lime | 0.00 | 0.00 | 7.37 | 0.45 | 2.18 | 0.00 | 0.00 | 0.00 | 0.00 |
| 23 | Citrus-Lime | 0.00 | 0.00 | 0.00 | 0.00 | 0.00 | 0.00 | 5.20 | 0.00 | 0.00 |
| 24 | Citrus-Mandarin | 0.05 | 0.00 | 0.00 | 0.00 | 0.00 | 1.86 | 0.00 | 0.00 | 0.00 |
| 25 | Citrus-Mandarin | 0.00 | 0.00 | 0.00 | 0.00 | 4.35 | 0.00 | 0.00 | 0.00 | 0.00 |
| 26 | Citrus-Mandarin | 0.00 | 0.00 | 0.00 | 0.00 | 0.00 | 0.00 | 0.00 | 0.00 | 0.00 |
| 27 | Citrus-Orange | 0.00 | 0.00 | 0.00 | 0.00 | 0.00 | 2.90 | 0.00 | 0.00 | 0.00 |
| 28 | Citrus-Orange | 3.79 | 0.00 | 0.00 | 0.00 | 4.35 | 23.05 | 0.00 | 0.00 | 0.00 |
| 29 | Citrus-Terpenic | 0.00 | 0.00 | 0.00 | 7.48 | 0.00 | 6.22 | 0.00 | 0.00 | 13.81 |
| 30 | Floral-Freesia | 6.96 | 4.05 | 7.37 | 0.00 | 10.85 | 24.87 | 10.38 | 0.00 | 14.96 |
| 31 | Floral-Jasmine | 7.59 | 0.58 | 22.85 | 20.96 | 24.65 | 7.46 | 1.66 | 8.76 | 1.78 |
| 32 | Floral-Lily of the valley | 6.06 | 0.00 | 3.98 | 0.45 | 3.48 | 0.00 | 5.20 | 0.00 | 0.00 |
| 33 | Floral-Medicinal | 0.00 | 0.00 | 0.00 | 0.01 | 0.06 | 0.00 | 0.00 | 0.00 | 0.00 |
| 34 | Floral-Medicinal | 0.00 | 0.00 | 0.00 | 0.03 | 0.06 | 0.00 | 0.00 | 0.00 | 0.00 |
| 35 | Floral-Medicinal | 0.00 | 0.00 | 0.00 | 0.00 | 0.00 | 0.00 | 0.00 | 0.00 | 0.00 |
| 36 | Floral-Medicinal | 0.00 | 0.00 | 0.00 | 0.00 | 0.00 | 0.00 | 0.00 | 0.00 | 0.00 |
| 37 | Floral-Orange flower | 0.00 | 0.00 | 0.22 | 0.01 | 0.00 | 0.00 | 0.00 | 0.00 | 0.00 |
| 38 | Floral-Orange flower | 0.00 | 0.00 | 0.00 | 0.00 | 0.00 | 0.00 | 0.00 | 0.00 | 0.00 |
| 39 | Floral-Orange flower | 0.00 | 0.00 | 0.15 | 0.00 | 0.00 | 0.00 | 0.00 | 0.00 | 0.00 |
| 40 | Floral-Orange flower | 0.00 | 0.00 | 0.00 | 0.00 | 0.00 | 0.00 | 0.00 | 0.00 | 0.00 |
| 41 | Floral-Orris | 0.00 | 0.58 | 0.00 | 5.98 | 1.16 | 0.19 | 0.00 | 0.18 | 0.58 |
| 42 | Floral-Rose | 5.75 | 0.00 | 2.95 | 3.29 | 2.61 | 8.95 | 10.39 | 0.00 | 1.15 |
| 43 | Floral-Solar | 0.82 | 2.90 | 0.00 | 7.48 | 4.35 | 4.97 | 0.00 | 0.00 | 0.00 |
| 44 | Fruity-Apple | 7.98 | 9.30 | 4.05 | 0.10 | 0.00 | 1.24 | 0.21 | 39.42 | 13.35 |
| 45 | Fruity-Banana | 0.00 | 0.00 | 2.21 | 0.00 | 0.15 | 0.02 | 0.00 | 3.51 | 28.42 |
| 46 | Fruity-Blackcurrant | 0.00 | 0.00 | 0.00 | 0.00 | 0.00 | 0.04 | 0.19 | 0.00 | 0.58 |
| 47 | Fruity-Candied fruit | 0.00 | 0.00 | 0.00 | 0.00 | 0.00 | 0.01 | 0.00 | 0.00 | 0.04 |
| 48 | Fruity-Candied fruit | 0.00 | 0.00 | 0.00 | 0.00 | 0.00 | 0.00 | 0.00 | 0.00 | 0.00 |
| 49 | Fruity-Candied fruit | 0.00 | 0.00 | 0.00 | 0.00 | 0.00 | 0.00 | 0.00 | 0.00 | 0.00 |
| 50 | Fruity-Candied fruit | 0.00 | 0.00 | 0.01 | 0.00 | 0.00 | 1.24 | 0.10 | 0.53 | 0.00 |
| 51 | Fruity-Candied fruit | 0.00 | 0.00 | 0.00 | 0.00 | 0.73 | 0.00 | 0.00 | 0.00 | 0.00 |
| 52 | Fruity-Coconut | 0.00 | 0.00 | 2.21 | 0.00 | 0.03 | 0.12 | 0.00 | 0.00 | 0.46 |
| 53 | Fruity-Liquor | 0.00 | 0.00 | 0.00 | 0.00 | 0.00 | 0.00 | 0.42 | 0.00 | 0.00 |
| 54 | Fruity-Melon | 0.05 | 0.00 | 0.00 | 0.00 | 0.00 | 0.06 | 0.00 | 0.00 | 0.00 |
| 55 | Fruity-Mushroom | 0.00 | 0.00 | 0.00 | 0.00 | 0.06 | 0.00 | 0.00 | 0.00 | 0.00 |
| 56 | Fruity-Nut | 0.00 | 0.00 | 0.00 | 0.00 | 0.00 | 0.00 | 0.00 | 0.00 | 0.00 |
| 57 | Fruity-Passionfruit | 0.02 | 0.00 | 0.00 | 0.00 | 0.00 | 0.25 | 0.00 | 0.00 | 0.00 |
| 58 | Fruity-Peach | 0.00 | 0.12 | 0.00 | 2.24 | 0.58 | 2.49 | 0.10 | 5.26 | 3.45 |
| 59 | Fruity-Pear | 0.00 | 0.00 | 2.28 | 0.00 | 0.00 | 1.18 | 0.00 | 8.76 | 6.91 |
| 60 | Fruity-Pineapple | 0.05 | 0.46 | 0.00 | 0.00 | 0.15 | 1.12 | 0.00 | 20.15 | 2.30 |
| 61 | Fruity-Raspberry | 0.13 | 0.00 | 1.11 | 0.00 | 0.00 | 0.00 | 0.00 | 0.35 | 0.00 |
| 62 | Fruity-Strawberry | 0.00 | 0.00 | 0.00 | 0.00 | 0.00 | 0.01 | 0.00 | 0.00 | 0.00 |
| 63 | Green-Cucumber | 0.00 | 0.00 | 0.66 | 0.00 | 0.00 | 0.00 | 0.00 | 0.00 | 0.00 |
| 64 | Green-Galbanum | 0.13 | 0.06 | 0.74 | 0.00 | 0.87 | 0.00 | 0.00 | 2.72 | 0.12 |
| 65 | Green-Grass | 0.31 | 0.58 | 0.00 | 0.00 | 0.44 | 0.37 | 0.42 | 5.78 | 0.00 |
| 66 | Green-Leaf | 0.31 | 0.58 | 0.22 | 0.25 | 3.34 | 0.00 | 3.12 | 4.40 | 0.23 |
| 67 | Green-Metallic | 0.00 | 0.00 | 0.00 | 0.00 | 0.00 | 0.00 | 0.00 | 0.00 | 0.00 |
| 68 | Green-Rhubarb | 1.26 | 0.00 | 0.88 | 0.75 | 10.16 | 2.49 | 2.08 | 0.00 | 0.00 |
| 69 | Green-Violet | 0.00 | 0.00 | 0.00 | 0.00 | 0.00 | 0.00 | 0.06 | 0.00 | 0.00 |
| 70 | Musk-Musk | 2.53 | 0.00 | 0.07 | 7.78 | 3.63 | 3.73 | 1.04 | 0.18 | 0.00 |
| 71 | Spicy-Cinnamon | 0.00 | 0.00 | 0.04 | 0.07 | 0.00 | 0.00 | 0.00 | 0.00 | 0.00 |
| 72 | Spice-Clove | 0.00 | 0.00 | 0.00 | 0.00 | 0.00 | 0.00 | 0.00 | 0.00 | 0.00 |
| 73 | Spice-Clove | 0.00 | 0.00 | 0.00 | 0.00 | 0.00 | 0.00 | 0.00 | 0.00 | 0.00 |
| 74 | Spice-Clove | 0.18 | 0.17 | 0.07 | 0.75 | 0.00 | 0.00 | 0.00 | 0.00 | 0.00 |

TABLE 4-continued

Composition based on odour descriptions of test perfume compositions 1 to 9

| | Ingredients | 1 | 2 | 3 | 4 | 5 | 6 | 7 | 8 | 9 |
|---|---|---|---|---|---|---|---|---|---|---|
| 75 | Spice-Clove | 1.15 | 0.00 | 0.00 | 0.00 | 0.29 | 0.00 | 0.00 | 0.00 | 0.00 |
| 76 | Spice-Clove | 0.00 | 0.00 | 0.00 | 0.00 | 0.00 | 0.00 | 0.00 | 0.00 | 0.00 |
| 77 | Spicy-Copaiba | 0.00 | 0.00 | 0.00 | 0.00 | 0.00 | 1.24 | 0.00 | 0.00 | 0.00 |
| 78 | Sweet-Almond | 0.00 | 0.00 | 0.00 | 0.00 | 0.00 | 0.00 | 0.00 | 0.00 | 0.35 |
| 79 | Sweet-Balsam | 0.00 | 0.00 | 0.00 | 0.00 | 0.00 | 0.00 | 0.00 | 0.00 | 0.00 |
| 80 | Sweet-Butter | 0.00 | 0.00 | 0.52 | 0.00 | 0.00 | 0.00 | 0.00 | 0.00 | 0.00 |
| 81 | Sweet-Cocoa | 0.00 | 0.00 | 0.00 | 0.00 | 0.00 | 0.00 | 0.00 | 0.00 | 0.00 |
| 82 | Sweet-Cooked sugar | 0.05 | 0.00 | 0.29 | 0.00 | 0.00 | 0.02 | 0.10 | 0.00 | 0.00 |
| 83 | Sweet-Heliotrope | 3.17 | 0.00 | 0.37 | 5.99 | 0.07 | 0.00 | 0.00 | 0.00 | 0.00 |
| 84 | Sweet-Milk Cream | 0.00 | 0.00 | 0.00 | 0.00 | 0.00 | 0.00 | 0.00 | 0.00 | 0.00 |
| 85 | Sweet-Molasses | 0.00 | 0.00 | 0.00 | 0.00 | 0.00 | 0.00 | 0.00 | 0.00 | 0.00 |
| 86 | Sweet-Tonka | 0.00 | 0.00 | 0.37 | 1.50 | 0.00 | 0.00 | 0.00 | 0.00 | 0.00 |
| 87 | Sweet-Tonka | 1.89 | 1.16 | 5.16 | 0.00 | 0.00 | 0.00 | 0.00 | 0.00 | 0.00 |
| 88 | Sweet-Tonka | 0.00 | 0.00 | 0.00 | 0.00 | 0.00 | 0.00 | 0.00 | 0.00 | 0.00 |
| 89 | Sweet-Vanilla | 0.24 | 0.00 | 1.47 | 1.80 | 0.06 | 0.00 | 0.00 | 0.00 | 0.00 |
| 90 | Watery-Sea water | 1.89 | 0.07 | 0.00 | 0.00 | 0.00 | 0.00 | 0.00 | 0.00 | 0.00 |
| 91 | Wood-Cedar | 6.32 | 8.11 | 4.42 | 15.86 | 1.63 | 0.00 | 0.00 | 0.00 | 0.00 |
| 92 | Woody-Moss | 0.95 | 0.00 | 0.00 | 0.00 | 0.15 | 0.00 | 0.00 | 0.00 | 0.00 |
| 93 | Woody-Patchouli | 10.11 | 0.81 | 0.96 | 0.75 | 0.00 | 0.00 | 0.00 | 0.00 | 0.00 |
| 94 | Woody-Sandalwood | 0.51 | 0.46 | 2.03 | 4.49 | 0.00 | 0.00 | 0.00 | 0.00 | 0.00 |
| 95 | Woody-Vetiver | 0.89 | 0.00 | 0.00 | 0.00 | 0.00 | 0.00 | 0.00 | 0.00 | 0.00 |

TABLE 5

Composition based on odour descriptions of test perfume compositions 10 to 18

| | Ingredients | 10 | 11 | 12 | 13 | 14 | 15 | 16 | 17 | 18 |
|---|---|---|---|---|---|---|---|---|---|---|
| 1 | Aldehydic-Aldehyde Zest | 0.00 | 0.69 | 0.00 | 0.00 | 0.04 | 1.61 | 0.00 | 0.00 | 0.0 |
| 2 | Aldehydic-Coriander Leaf | 0.00 | 0.00 | 0.00 | 0.00 | 0.00 | 0.05 | 0.00 | 0.00 | 0.0 |
| 3 | Aldehydic-Mandarin | 0.00 | 0.00 | 0.00 | 0.00 | 0.00 | 0.00 | 0.00 | 0.00 | 0.0 |
| 4 | Amber-Amber Dry | 0.00 | 0.00 | 0.00 | 0.00 | 0.00 | 0.00 | 0.10 | 0.00 | 0.0 |
| 5 | Amber-Ambergris | 0.00 | 0.08 | 0.07 | 0.00 | 0.05 | 0.00 | 0.37 | 0.00 | 0.0 |
| 6 | Animalic-Fecal | 0.04 | 0.00 | 0.06 | 0.02 | 0.00 | 0.06 | 0.01 | 0.00 | 0.0 |
| 7 | Animalic-Leather | 0.00 | 0.00 | 0.00 | 0.00 | 0.00 | 0.00 | 0.00 | 0.00 | 0.0 |
| 8 | Aromatic herbal-Anis Tarragon | 0.00 | 0.00 | 0.07 | 0.00 | 0.00 | 0.38 | 0.00 | 0.00 | 0.0 |
| 9 | Aromatic herbal-Armoise | 0.00 | 0.00 | 0.00 | 0.00 | 0.00 | 0.00 | 0.00 | 0.00 | 0.0 |
| 10 | Aromatic herbal-Caraway Seed | 0.00 | 0.08 | 0.00 | 0.00 | 0.00 | 0.00 | 0.00 | 0.00 | 0.0 |
| 11 | Aromatic herbal-Coniferous | 0.00 | 0.00 | 0.00 | 0.00 | 0.00 | 0.00 | 0.00 | 0.00 | 0.0 |
| 12 | Aromatic herbal-Eucalyptus | 0.00 | 0.77 | 0.00 | 0.00 | 0.00 | 0.00 | 0.00 | 0.00 | 0.0 |
| 13 | Aromatic herbal-Lavender | 0.00 | 9.08 | 3.24 | 0.00 | 0.01 | 0.00 | 9.95 | 0.00 | 0.0 |
| 14 | Aromatic herbal-Peppermint | 0.00 | 0.00 | 0.00 | 0.00 | 0.00 | 0.00 | 0.00 | 0.00 | 0.0 |
| 15 | Aromatic herbal-Thyme | 0.00 | 0.08 | 0.00 | 0.00 | 0.00 | 0.00 | 0.01 | 0.00 | 0.0 |
| 16 | Citrus-Grapefruit | 0.00 | 0.00 | 0.00 | 0.00 | 0.00 | 0.00 | 1.47 | 0.00 | 0.0 |
| 17 | Citrus-Lemon | 0.50 | 0.00 | 0.00 | 3.80 | 1.54 | 0.00 | 0.00 | 0.00 | 0.0 |
| 18 | Citrus-Lime | 0.20 | 0.00 | 0.00 | 0.00 | 0.00 | 0.00 | 0.00 | 0.00 | 0.0 |
| 19 | Citrus-Lime | 0.00 | 0.00 | 0.00 | 0.00 | 0.00 | 0.00 | 0.18 | 0.00 | 0.0 |
| 20 | Citrus-Lime | 0.00 | 0.00 | 0.00 | 0.00 | 0.00 | 0.00 | 0.37 | 0.00 | 0.0 |
| 21 | Citrus-Lime | 0.93 | 0.00 | 0.00 | 0.00 | 0.00 | 0.00 | 0.00 | 0.00 | 0.0 |
| 22 | Citrus-Lime | 0.00 | 0.77 | 0.00 | 0.63 | 5.14 | 4.75 | 0.00 | 0.00 | 0.0 |
| 23 | Citrus-Lime | 0.00 | 0.00 | 0.00 | 0.00 | 0.00 | 0.00 | 0.00 | 0.00 | 0.0 |
| 24 | Citrus-Mandarin | 0.00 | 0.00 | 0.00 | 0.00 | 0.00 | 0.00 | 0.00 | 0.00 | 0.0 |
| 25 | Citrus-Mandarin | 0.00 | 0.00 | 0.00 | 0.00 | 0.00 | 0.00 | 0.00 | 0.00 | 0.0 |
| 26 | Citrus-Mandarin | 0.00 | 0.00 | 0.00 | 0.38 | 0.00 | 0.00 | 0.00 | 0.00 | 0.0 |
| 27 | Citrus-Orange | 0.00 | 0.00 | 0.00 | 0.00 | 0.00 | 0.00 | 0.00 | 0.00 | 0.0 |
| 28 | Citrus-Orange | 6.64 | 0.00 | 0.00 | 0.00 | 0.51 | 0.00 | 0.00 | 0.00 | 0.0 |
| 29 | Citrus-Terpenic | 0.00 | 0.00 | 0.00 | 0.00 | 0.00 | 0.00 | 0.00 | 0.00 | 0.0 |
| 30 | Floral-Freesia | 13.50 | 6.92 | 9.70 | 2.12 | 5.14 | 7.59 | 17.60 | 0.00 | 0.0 |
| 31 | Floral-Jasmine | 31.02 | 34.59 | 18.46 | 8.83 | 33.94 | 12.34 | 8.97 | 0.00 | 0.0 |
| 32 | Floral-Lily of the valley | 3.70 | 7.23 | 11.00 | 6.94 | 1.65 | 5.03 | 9.47 | 0.00 | 0.0 |
| 33 | Floral-Medicinal | 0.00 | 0.00 | 0.00 | 0.00 | 0.00 | 0.00 | 0.00 | 0.00 | 0.0 |
| 34 | Floral-Medicinal | 0.00 | 0.00 | 0.00 | 0.00 | 0.00 | 0.00 | 0.00 | 0.00 | 0.0 |
| 35 | Floral-Medicinal | 0.10 | 0.00 | 0.00 | 0.00 | 0.00 | 0.00 | 0.00 | 0.00 | 0.0 |
| 36 | Floral-Medicinal | 1.20 | 0.62 | 0.00 | 0.00 | 0.00 | 0.00 | 0.00 | 0.00 | 0.0 |
| 37 | Floral-Orange flower | 0.80 | 0.08 | 0.00 | 0.00 | 0.00 | 0.00 | 0.07 | 0.00 | 0.0 |
| 38 | Floral-Orange flower | 0.00 | 0.00 | 0.00 | 0.76 | 0.00 | 0.00 | 0.00 | 0.00 | 0.0 |
| 39 | Floral-Orange flower | 0.00 | 0.77 | 0.00 | 0.00 | 0.00 | 0.00 | 0.02 | 0.00 | 0.0 |
| 40 | Floral-Orange flower | 0.00 | 0.00 | 0.00 | 0.00 | 0.00 | 0.00 | 0.18 | 0.00 | 0.0 |
| 41 | Floral-Orris | 0.40 | 6.00 | 0.65 | 1.91 | 3.11 | 3.80 | 6.49 | 0.00 | 0.0 |

TABLE 5-continued

Composition based on odour descriptions of test perfume compositions 10 to 18

| | Ingredients | Test Perfume Compositions | | | | | | | | |
|---|---|---|---|---|---|---|---|---|---|---|
| | | 10 | 11 | 12 | 13 | 14 | 15 | 16 | 17 | 18 |
| 42 | Floral-Rose | 0.00 | 6.77 | 6.80 | 15.32 | 4.22 | 26.12 | 2.58 | 0.00 | 0.0 |
| 43 | Floral-Solar | 14.00 | 3.08 | 6.47 | 0.00 | 12.34 | 9.02 | 4.05 | 0.00 | 0.0 |
| 44 | Fruity-Apple | 0.30 | 2.31 | 17.15 | 0.00 | 0.51 | 5.98 | 3.01 | 0.00 | 0.0 |
| 45 | Fruity-Banana | 0.00 | 5.42 | 0.00 | 0.00 | 2.36 | 5.69 | 0.00 | 0.00 | 0.0 |
| 46 | Fruity-Blackcurrant | 0.20 | 0.00 | 1.62 | 0.00 | 2.57 | 0.00 | 0.29 | 0.00 | 0.0 |
| 47 | Fruity-Candied fruit | 0.00 | 0.08 | 0.07 | 0.00 | 0.00 | 0.00 | 0.17 | 0.00 | 0.0 |
| 48 | Fruity-Candied fruit | 0.00 | 0.00 | 0.00 | 0.00 | 0.21 | 0.00 | 0.00 | 0.00 | 0.0 |
| 49 | Fruity-Candied fruit | 0.00 | 0.00 | 0.00 | 0.00 | 0.21 | 0.00 | 0.00 | 0.00 | 0.0 |
| 50 | Fruity-Candied fruit | 0.10 | 0.00 | 0.00 | 0.00 | 0.21 | 0.00 | 0.00 | 0.00 | 0.0 |
| 51 | Fruity-Candied fruit | 0.00 | 0.00 | 0.00 | 0.00 | 0.00 | 0.00 | 0.00 | 0.00 | 0.0 |
| 52 | Fruity-Coconut | 0.15 | 0.00 | 0.00 | 0.00 | 0.00 | 0.09 | 0.01 | 1.50 | 0.0 |
| 53 | Fruity-Liquor | 0.20 | 0.00 | 0.00 | 0.00 | 0.00 | 0.00 | 0.00 | 0.00 | 0.0 |
| 54 | Fruity-Melon | 0.00 | 0.00 | 0.87 | 0.00 | 0.00 | 0.00 | 0.00 | 0.00 | 0.0 |
| 55 | Fruity-Mushroom | 0.00 | 0.00 | 0.00 | 0.00 | 0.00 | 0.00 | 0.00 | 0.00 | 0.0 |
| 56 | Fruity-Nut | 0.00 | 0.00 | 0.00 | 0.00 | 0.00 | 0.00 | 0.00 | 0.03 | 0.0 |
| 57 | Fruity-Passionfruit | 0.00 | 0.00 | 0.00 | 0.00 | 0.00 | 0.00 | 0.00 | 0.00 | 0.0 |
| 58 | Fruity-Peach | 4.70 | 0.31 | 1.62 | 0.00 | 0.82 | 0.66 | 0.88 | 0.00 | 0.0 |
| 59 | Fruity-Pear | 0.40 | 1.38 | 0.00 | 0.25 | 0.01 | 0.00 | 0.01 | 0.00 | 0.0 |
| 60 | Fruity-Pineapple | 1.20 | 0.38 | 0.00 | 0.00 | 0.00 | 0.00 | 0.30 | 0.00 | 0.0 |
| 61 | Fruity-Raspberry | 3.00 | 0.00 | 0.00 | 0.00 | 0.00 | 0.00 | 0.00 | 0.00 | 0.0 |
| 62 | Fruity-Strawberry | 0.80 | 0.00 | 0.00 | 0.00 | 0.11 | 0.00 | 0.00 | 0.00 | 0.0 |
| 63 | Green-Cucumber | 2.50 | 1.23 | 12.22 | 0.00 | 0.00 | 0.00 | 0.00 | 0.00 | 0.0 |
| 64 | Green-Galbanum | 0.00 | 0.00 | 1.13 | 0.00 | 0.06 | 0.48 | 0.09 | 0.00 | 0.0 |
| 65 | Green-Grass | 0.80 | 0.00 | 0.16 | 0.00 | 0.01 | 0.00 | 0.18 | 0.00 | 0.0 |
| 66 | Green-Leaf | 1.00 | 1.23 | 0.49 | 0.00 | 0.10 | 0.19 | 0.92 | 0.00 | 0.0 |
| 67 | Green-Metallic | 0.00 | 0.77 | 0.00 | 0.00 | 0.00 | 0.28 | 0.00 | 0.00 | 0.0 |
| 68 | Green-Rhubarb | 0.10 | 0.77 | 0.00 | 0.00 | 0.21 | 1.90 | 0.46 | 0.00 | 0.0 |
| 69 | Green-Violet | 0.00 | 0.00 | 0.00 | 0.06 | 0.00 | 0.00 | 0.12 | 0.00 | 0.0 |
| 70 | Musk-Musk | 2.50 | 0.31 | 6.47 | 36.02 | 23.65 | 0.47 | 4.09 | 0.00 | 0.0 |
| 71 | Spicy-Cinnamon | 0.00 | 0.00 | 0.00 | 0.00 | 0.00 | 0.00 | 0.00 | 0.00 | 0.0 |
| 72 | Spice-Clove | 0.00 | 0.00 | 0.00 | 0.00 | 0.00 | 1.42 | 0.00 | 0.00 | 0.0 |
| 73 | Spice-Clove | 0.00 | 0.00 | 0.00 | 0.00 | 0.00 | 0.00 | 0.00 | 0.00 | 0.0 |
| 74 | Spice-Clove | 0.00 | 0.00 | 0.00 | 0.00 | 0.00 | 0.00 | 0.00 | 0.00 | 0.0 |
| 75 | Spice-Clove | 0.00 | 0.00 | 0.00 | 0.00 | 0.00 | 0.00 | 0.00 | 0.00 | 0.0 |
| 76 | Spice-Clove | 0.00 | 0.15 | 0.00 | 0.13 | 0.00 | 0.00 | 0.00 | 0.00 | 0.0 |
| 77 | Spicy-Copaiba | 0.00 | 0.00 | 0.00 | 0.00 | 0.00 | 0.00 | 0.00 | 0.00 | 0.0 |
| 78 | Sweet-Almond | 0.00 | 0.00 | 0.00 | 0.00 | 0.21 | 0.00 | 0.00 | 0.00 | 0.0 |
| 79 | Sweet-Balsam | 0.00 | 0.00 | 0.00 | 0.00 | 0.00 | 0.95 | 0.00 | 0.00 | 0.0 |
| 80 | Sweet-Butter | 0.02 | 0.00 | 0.00 | 0.00 | 0.00 | 0.00 | 0.00 | 18.26 | 0.0 |
| 81 | Sweet-Cocoa | 0.00 | 0.00 | 0.00 | 0.00 | 0.00 | 0.00 | 0.00 | 59.85 | 0.0 |
| 82 | Sweet-Cooked sugar | 0.60 | 0.00 | 0.00 | 0.00 | 0.00 | 0.00 | 3.78 | 2.39 | 11.8 |
| 83 | Sweet-Heliotrope | 1.50 | 2.31 | 0.00 | 0.63 | 0.00 | 1.14 | 0.00 | 2.00 | 0.0 |
| 84 | Sweet-Milk Cream | 0.00 | 0.00 | 0.00 | 0.00 | 0.00 | 0.00 | 0.00 | 1.50 | 0.0 |
| 85 | Sweet-Molasses | 0.00 | 0.00 | 0.00 | 0.00 | 0.00 | 0.00 | 0.00 | 0.00 | 49.0 |
| 86 | Sweet-Tonka | 0.00 | 0.00 | 0.00 | 0.00 | 0.00 | 0.00 | 0.00 | 1.50 | 0.0 |
| 87 | Sweet-Tonka | 0.00 | 0.00 | 0.00 | 0.00 | 0.00 | 1.42 | 0.92 | 0.00 | 0.0 |
| 88 | Sweet-Tonka | 0.00 | 0.02 | 0.00 | 0.00 | 0.00 | 0.00 | 0.00 | 0.00 | 0.0 |
| 89 | Sweet-Vanilla | 0.90 | 0.18 | 0.00 | 2.40 | 0.00 | 0.28 | 5.25 | 14.97 | 39.2 |
| 90 | Watery-Sea water | 0.00 | 0.00 | 0.06 | 0.00 | 0.00 | 0.00 | 0.07 | 0.00 | 0.0 |
| 91 | Wood-Cedar | 6.00 | 4.77 | 0.00 | 19.80 | 1.03 | 7.59 | 14.83 | 0.00 | 0.0 |
| 92 | Woody-Moss | 0.00 | 0.00 | 0.00 | 0.00 | 0.03 | 0.09 | 0.15 | 0.00 | 0.0 |
| 93 | Woody-Patchouli | 0.00 | 0.00 | 0.00 | 0.00 | 0.00 | 0.05 | 2.58 | 0.00 | 0.0 |
| 94 | Woody-Sandalwood | 0.00 | 0.77 | 1.62 | 0.00 | 0.00 | 0.57 | 0.00 | 0.00 | 0.0 |
| 95 | Woody-Vetiver | 0.00 | 0.00 | 0.00 | 0.00 | 0.00 | 0.00 | 0.00 | 0.00 | 0.0 |

TABLE 6

Ingredients used in test perfume compositions 1 to 18

| | Ingredients in Tables 4 and 5 | Ingredient selection |
|---|---|---|
| 1 | Aldehydic-Aldehyde Zest | octanal, nonanal, decanal, undecanal, dodecanal, undec-10-enal, 2-methylundecanal, (E)-dodec-2-enal, or mixtures thereof |
| 2 | Aldehydic-Coriander Leaf | (E)-dec-2-enal, (E)-tridec-2-enenitrile or mixtures thereof |
| 3 | Aldehydic-Mandarin | dodecanenitrile |
| 4 | Amber-Amber Dry | decahydro-2,2,6,6,7,8,8-heptamethyl indenofuran, 1-(2,2,6-trimethylcyclohexyl)hexan-3-ol, 1-(2,2,6-trimethylcyclohexyl)hexan-3-ol, 2,2,6-trimethylcyclohexyl-3-hexanol, or mixtures thereof |
| 5 | Amber-Ambergris | 3,8,8,11a-tetramethyldodecahydro-1H-3,5a-epoxynaphtho[2,1-c]oxepine, (3aR,5aS,9aS,9bR)-3a,6,6,9a-tetramethyl-2,4,5,5a,7,8,9,9b-octahydro-1H-benzo[e][1]benzofuran, (ethoxymethoxy)cyclododecane, 3a-ethyl-6,6,9a-trimethyldodecahydronaphtho[1,2-c]furan, 2,4-dimethyl-2-(5,5,8,8-tetramethyl-5,6,7,8-tetrahydronaphthalen-2-yl)-1,3-dioxolane, or mixtures thereof |

TABLE 6-continued

Ingredients used in test perfume compositions 1 to 18

| Ingredients in Tables 4 and 5 | Ingredient selection |
|---|---|
| 6 Animalic-Fecal | 1H-indole, 8,8-di(1H-indol-3-yl)-2,6-dimethyloctan-2-ol, or mixtures thereof |
| 7 Animalic-Leather | 6-(sec-butyl)quinoline, 6-butan-2-ylquinoline, 2-(2-methylpropyl)quinoline or mixtures thereof |
| 8 Aromatic herbal-Anis Tarragon | (E)-1-methoxy-4-(prop-1-en-1-yl)benzene, 1-allyl-4-methoxybenzene, 1-(cyclopropylmethyl)-4-methoxybenzene, or mixtures thereof |
| 9 Aromatic herbal-Armoise | armoise oil, cedar leaf oil, (Z)-1-(cyclooct-3-en-1-yl)ethanone, or mixtures thereof |
| 10 Aromatic herbal-Caraway Seed | (5R)-2-methyl-5-prop-1-en-2-ylcyclohex-2-en-1-one |
| 11 Aromatic herbal-Coniferous | (2S,4S)-1,7,7-trimethylbicyclo[2.2.1]heptan-2-yl acetate, 2,6,6-trimethylbicyclo[3.1.1]hept-2-ene, 2-(tert-butyl)cyclohexanol, or mixtures thereof |
| 12 Aromatic herbal-Eucalyptus | (1s,4s)-1,3,3-trimethyl-2-oxabicyclo[2.2.2]octane, or mixtures thereof |
| 13 Aromatic herbal-Lavender | cardamom oil, 2,6-dimethyloct-7-en-2-ol, 6-methylheptan-3-one heptan-2-one, lavandin oil, lavandin reconstitution, 3,7-dimethylocta-1,6-dien-3-yl acetate, octan-2-one, 3,7-dimethylocta-1,6-dien-3-yl dimethylcarbamate, 2-(4-methylcyclohex-3-en-1-yl)propan-2-yl acetate, or mixtures thereof |
| 14 Aromatic herbal-Peppermint | 2-(sec-butyl)cyclohexanone, 2-isopropyl-5-methylcyclohexanol, 2-isopropyl-5-methylcyclohexanone, mint oil, peppermint oil, or mixtures thereof |
| 15 Aromatic herbal-Thyme | (1S,2S,4S)-1,7,7-trimethylbicyclo[2.2.1]heptan-2-ol, (1S,4S)-1,7,7-trimethylbicyclo[2.2.1]heptan-2-one, 2-isopropyl-5-methylphenol, or mixtures thereof |
| 16 Citrus-Grapefruit | 6,6-dimethoxy-2,5,5-trimethylhex-2-ene, grapefruit oil, or mixtures thereof |
| 17 Citrus-Lemon | bergamote reconstitution, (E)-3,7-dimethylocta-2,6-dienal, lemon oil, lemon oil reconstitution, (2E,6Z)-3,7-dimethylnona-2,6-dienenitrile, litsea cubeba oil, or mixtures thereof |
| 18 Citrus-Lime | 1-methyl-4-propan-2-ylbenzene |
| 19 Citrus-Lime | elemi oil |
| 20 Citrus-Lime | elemi resinoid |
| 21 Citrus-Lime | lime oxide |
| 22 Citrus-Lime | 2-(4-methylcyclohex-3-en-1-yl)propan-2-ol |
| 23 Citrus-Lime | 1-methyl-4-(propan-2-ylidene)cyclohex-1-ene |
| 24 Citrus-Mandarin | methyl 2-(methylamino)benzoate |
| 25 Citrus-Mandarin | madarin oil |
| 26 Citrus-Mandarin | tamarin reconstitution |
| 27 Citrus-Orange | grapefruit oil |
| 28 Citrus-Orange | orange oil |
| 29 Citrus-Terpenic | grapefruit terpenes, orange terpenes, or mixtures thereof |
| 30 Floral-Freesia | 2-methyl-4-phenylbutan-2-ol, 2,6-dimethylheptan-2-ol, (E)-3,7-dimethylnona-1,6-dien-3-ol, 3,7-dimethyloctan-3-ol, or mixtures thereof |
| 31 Floral-Jasmine | (Z)-2-benzylideneheptanal, benzyl acetate, rose oxide, 3-methyl-2-pentylcyclopent-2-enone, methyl 3-oxo-2-pentylcyclopentaneacetate, (E)-2-benzylideneoctanal, 2-hexylcyclopent-2-enone, (Z)-3-methyl-2-(pent-2-en-1-yl)cyclopent-2-enone, or mixtures thereof |
| 32 Floral-Lily of the valley | 3-(4-(tert-butyl)phenyl)propanal, 4-cyclohexyl-2-methylbutan-2-ol, 3-(4-isopropylphenyl)-2-methylpropanal, 4-(4-hydroxy-4-methylpentyl)cyclohex-3-enecarbaldehyde, 3-(4-ethylphenyl)-2,2-dimethylpropanal, 3-(3-isopropylphenyl)butanal, tetrahydro-4-methyl-2-(2-methylpropyl)-2H-pyran-4-ol, lily of the valey reconstitution, 3-(4-(tert-butyl)phenyl)-2-methylpropanal, (4-isopropylcyclohexyl)methanol, 3-(benzo[d][1,3]dioxol-5-yl)-2-methylpropanal, (E)-methyl 2-((3-(4-(tert-butyl)phenyl)-2-methylprop-1-en-1-yl)amino)benzoate, or mixtures thereof |
| 33 Floral-Medicinal | 1-methoxy-4-methylbenzene |
| 34 Floral-Medicinal | methyl benzoate |
| 35 Floral-Medicinal | methyl 2-hydroxybenzoate |
| 36 Floral-Medicinal | 2-methoxynaphtalene |
| 37 Floral-Orange flower | methyl 2-aminobenzoate |
| 38 Floral-Orange flower | orange flower reconstitution |
| 39 Floral-Orange flower | 1-(2-naphtalenyl)-ethanone |
| 40 Floral-Orange flower | orange flower reconstitution |
| 41 Floral-Orris | (E)-4-(2,6,6-trimethylcyclohex-1-en-1-yl)but-3-en-2-one, (E)-4-(2,6,6-trimethylcyclohex-2-en-1-yl)but-3-en-2-one, (E)-4-(2,5,6,6-tetramethylcyclohex-2-en-1-yl)but-3-en-2-one, (E)-3-methyl-4-(2,6,6-trimethylcyclohex-2-en-1-yl)but-3-en-2-one, (Z)-3,4,5,6,6-pentamethylhept-3-en-2-one, Orris reconstitution, or mixtures thereof |
| 42 Floral-Rose | 3,7-dimethyloct-6-en-1-ol, 3,7-dimethyloct-6-en-1-yl acetate, damascenia reconstitution, 2-methyl-1-phenylpropan-2-yl acetate, 2-methyl-1-phenylpropan-2-yl butanoate, oxydibenzene, (E)-3,7-dimethylocta-2,6-dien-1-ol, geranium reconstitution, geranium oil, (E)-3,7-dimethylocta-2,6-dien-1-yl acetate, 2,4-dimethyl-4,4a,5,9b-tetrahydroindeno[1,2-d][1,3]dioxine, (2Z)-3,7-dimethylocta-2,6-dien-1-ol, (Z)-3,7-dimethylocta-2,6-dien-1-yl acetate, 3,7-dimethyloctan-1-ol, 2-cyclohexylidene-2-phenylacetonitrile, 2-cyclohexylidene-2-(o-tolyl)acetonitrile, 2-phenylethyl acetate, 2-phenylethanol, 2-phenylethyl 2-phenylacetate, 2,2-dimethyl-2-pheylethyl propionate2,2,2-trichloro-1-phenylethyl acetate, or mixtures thereof; |
| 43 Floral-Solar | pentyl 2-hydroxybenzoate, benzyl 2-hydroxybenzoate, cyclohexyl 2-hydroxybenzoate, (Z)-hex-3-en-1-yl 2-hydroxybenzoate, hexyl 2-hydroxybenzoate, ylang reconstitution, or mixtures thereof |
| 44 Fruity-Apple | 2-(tert-butyl)cyclohexyl acetate, apple reconstitution, diethyl propanedioate, ethyl 3-oxobutanoate, ethyl 2-methylbutanoate, ethyl 2-(2-methyl-1,3-dioxolan-2-yl)acetate, (E)-hex-2-enal, isopropyl 2-methylbutanoate, (Z)-hex-3-en-1-yl methyl carbonate, ethyl 2-methylpentanoate, green apple reconstitution, or mixtures thereof |
| 45 Fruity-Banana | butyl acetate, (3aR,6S,7aS)-3a,4,5,6,7,7a-hexahydro-1H-4,7-methanoinden-6-yl propionate, 3-methylbutyl acetate, 3-methylbutyl butanoate, (3aR,6S,7aS)-3a,4,5,6,7,7a-hexahydro-1H-4,7-methanoinden-6-yl acetate, 6-methylhept-5-en-2-one. 3-methylbut-2-en-1-yl acetate, or mixtures thereof |
| 46 Fruity-Blackcurrant | blackcurrent reconstitution, (3E,6E)-2,4,4,7-tetramethylnona-6,8-dien-3-one oxime, 2-(4-methylcyclohex-3-en-1-yl)propane-2-thiol, 5-methyl-2(2-methylethyl)-cyclohexanone, or mixtures thereof |
| 47 Fruity-Candied fruit | (E)-1-(2,6,6-trimethylcyclohexa-1,3-dien-1-yl)but-2-en-1-one |
| 48 Fruity-Candied fruit | (E)-1-(2,6,6-trimethylcyclohex-2-en-1-yl)but-2-en-1-one |
| 49 Fruity-Candied fruit | (E)-1-(2,6,6-trimethyl-1-cyclohexenyl)but-2-en-1-one |
| 50 Fruity-Candied fruit | 1-(2,6,6-trimethyl-1-cyclohex-3-enyl)but-2-en-1-one |
| 51 Fruity-Candied fruit | ethyl 2-ethyl-6,6-dimethylcyclohex-2-enecarboxylate |

TABLE 6-continued

Ingredients used in test perfume compositions 1 to 18

| Ingredients in Tables 4 and 5 | Ingredient selection |
|---|---|
| 52 Fruity-Coconut | 6-pentyltetrahydro-2H-pyran-2-one, (E)-6-(pent-3-en-1-yl)tetrahydro-2H-pyran-2-one, 8-methyl-1-oxaspiro[4.5]decan-2-one, 6-propyltetrahydro-2H-pyran-2-one, 5-pentyldihydrofuran-2(3H)-one, or mixtures thereof |
| 53 Fruity-Liquor | ethyl octanoate, ethyl propionate, or mixtures thereof |
| 54 Fruity-Melon | 2,6-dimethylhept-5-enal |
| 55 Fruity-Mushroom | 1-(3,3-dimethylcyclohexyl)ethyl formate |
| 56 Fruity-Nut | (E)-5-methylhept-2-en-4-one |
| 57 Fruity-Passionfruit | 2-methyl-4-propyl-1,3-oxathiane |
| 58 Fruity-Peach | 5-hexyloxolan-2-one, 5-heptyldihydrofuran-2(3H)-one, 2,2,5-trimethyl-5-pentylcyclopentanone, or mixtures thereof; |
| 59 Fruity-Pear | hexyl 2-methylbutanoate, ethyl acetate, (2E,4Z)-ethyl deca-2,4-dienoate, (Z)-hex-3-en-1-yl acetate, hexyl acetate, or mixtures thereof |
| 60 Fruity-Pineapple | allyl caproate, allyl cyclohexylpropionate, allyl heptanoate, pentyl buanoate, ethyl hexanoate, ethyl heptanoate, or mixtures thereof |
| 61 Fruity-Raspberry | 4-(4-hydroxyphenyl)butan-2-one |
| 62 Fruity-Strawberry | ethyl butanoate, ethyl 3-phenyloxirane-2-carboxylate, methyl 3-phenylprop-2-enoate, ethyl methyl phenyl glycidate, or mixtures thereof |
| 63 Green-Cucumber | (E)-4-methyldec-3-en-5-ol |
| 64 Green-Galbanum | prop-2-enyl 2-(3-methylbutoxy)acetate, (2-(isopentyloxy)ethyl)benzene, allyl 2-(cyclohexyloxy)acetate, 1-(5,5-dimethylcyclohex-1-en-1-yl)pent-4-en-1-one, 2-cyclohexylhepta-1,6-dien-3-one, or mixtures thereof |
| 65 Green-Grass | hexan-1-ol, (Z)-hex-3-en-1-ol, (Z)-hex-3-en-1-yl 2-methylpropanoate, or mixtures thereof |
| 66 Green-Leaf | hexanal, 2,4-dimethylcyclohex-3-ene-1-carbaldehyde, hexyl benzoate, 2,4,6-trimethylcyclohex-3-enecarbaldehyde, bicyclo[2.2.2]oct-5-ene-2-carboxaldehyde, (E)-5-methylheptan-3-one oxime, 2,4-dimethylcyclohex-3-enecarbaldehyde, or mixtures thereof |
| 67 Green-Metallic | 4-methyl-2-(2-methylprop-1-en-1-yl)tetrahydro-2H-pyran, or mixtures thereof |
| 68 Green-Rhubarb | 1-phenylethyl acetate, 2,4-dimethyl-4-phenyltetrahydrofuran, or mixtures thereof |
| 69 Green-Violet | (E)-non-2-enal, methyl non-2-ynoate, (E)-methyl non-2-enoate, or mixtures thereof |
| 70 Musk | (Z)-oxacycloheptadec-10-en-2-one, (Z)-3-methylcyclotetradec-5-enone, 1,4-dioxacycloheptadecane-5,17-dione, (E)-oxacyclohexadec-12-en-2-one, 1a,3,3,4,6,6-hexamethyl-1a,2,3,4,5,6,7,7a-octahydronaphtho[2,3-b]oxirene, (E)-13-methyloxacyclopentadec-10-en-2-one, 2-(1-(3,3-dimethylcyclohexyl)ethoxy)-2-methylpropyl cyclopropanecarboxylate, cyclopentadecanone, hexadecanolide, (E)-2-((3,5-dimethylhex-3-en-2-yl)oxy)-2-methylpropyl cyclopropanecarboxylate, oxacyclohexadecan-2-one, (Z)-3-methylcyclopentadec-5-enone, or mixtures thereof |
| 71 Spicy-Cinnamon | octyl formate |
| 72 Spice-Clove | clove oil |
| 73 Spice-Clove | 2-methoxy-4-propylphenol |
| 74 Spice-Clove | 4-allyl-2-methoxyphenol |
| 75 Spice-Clove | 4-allyl-2-methoxyphenyl acetate |
| 76 Spice-Clove | (E)-2-methoxy-4-(prop-1-en-1-yl)phenol |
| 77 Spicy-Copaiba | (Z)-4,11,11-trimethyl-8-methylenebicyclo[7.2.0]undec-4-ene |
| 78 Sweet-Almond | benzaldehyde |
| 79 Sweet-Balsam | (E)-3-phenylprop-2-en-1-ol |
| 80 Sweet-Butter | 3-hydroxybutan-2-one, 2,3-pentadione, 1-butoxy-1-oxopropan-2-yl butanoate, decenoic acid, or mixtures thereof |
| 81 Sweet-Cocoa | black chocolate reconstitution |
| 82 Sweet-Cooked sugar | 2-ethyl-3-hydroxy-4H-pyran-4-one, 2-ethyl-4-hydroxy-5-methylfuran-3(2H)-one, 3-hydroxy-2-methyl-4, or mixtures thereof |
| 83 Sweet-Heliotrope | 4-methoxybenzaldehyde, benzo[d][1,3]dioxole-5-carbaldehyde, or mixtures thereof |
| 84 Sweet-Milk Cream | 4-ethyl-5-methylthiazol-2-ol, 2-(4-Methyl-1,3-thiazol-5-yl)ethanol, or mixtures thereof |
| 85 Sweet-Molasses | 3-hydroxy-4,5-dimethylfuran-2(5H)-one, 2-hydroxy-3-methylcyclopent-2-enone, or mixtures thereof |
| 86 Sweet-Tonka | octahydro-2H-chromen-2-one |
| 87 Sweet-Tonka | 2H-chromen-2-one |
| 88 Sweet-Tonka | 4-methylbenzaldehyde |
| 89 Sweet-Vanilla | 3-ethoxy-4-hydroxybenzaldehyde, 2-methoxyphenol, 4-formyl-2-methoxyphenyl 2-methylpropanoate, 4-hydroxy-3-methoxybenzaldehyde, 3,4-dimethoxybenzaldehyde, or mixtures thereof |
| 90 Watery-Sea water | 2,6,10-trimethylundec-9-enal, 7-isopentyl-2H-benzo[b][1,4]dioxepin-3(4H)-one, 8-methyl-1,5-benzodioxepin-3-one, 1-methyl-4-(4-methylpent-3-en-1-yl)cyclohex-3-enecarbaldehyde, or mixtures thereof |
| 91 Wood-Cedar | 4-(tert-butyl)cyclohexyl acetate, (1S,6R,8aR)-1,4,4,6-tetramethyloctahydro-1H-5,8a-methanoazulen-6-ol, (1S,6R,8aR)-1,4,4,6-tetramethyloctahydro-1H-5,8a-methanoazulen-6-yl acetate, (1R,6S,8aS)-6-methoxy-1,4,4,6-tetramethyloctahydro-1H-5,8a-methanoazulene, 2-(tert-pentyl)cyclohexyl acetate, 1-(2,3,8,8-tetramethyl-1,2,3,4,5,6,7,8-octahydronaphthalen-2-yl)ethanone, 1-(2,3,8,8-tetramethyl-1,2,3,4,5,6,7,8-octahydronaphthalen-2-yl)ethanone, 1-((1S,8aS)-1,4,4,6-tetramethyl-2,3,3a,4,5,8-hexahydro-1H-5,8a-methanoazulen-7-yl)ethanone, or mixtures thereof |
| 92 Woody-Moss | methyl 2,4-dihydroxy-3,6-dimethylbenzoate |
| 93 Woody-Patchouli | patchouli oil, 1,1,2,3,3-pentamethyl-2,3,6,7-tetrahydro-1H-inden-4(5H)-one, or mixtures thereof |
| 94 Woody-Sandalwood | (E)-3-methyl-5-(2,2,3-trimethylcyclopent-3-en-1-yl)pent-4-en-2-ol, (1-methyl-2-((1,2,2-trimethylbicyclo[3.1.0]hexan-3-yl)methyl)cyclopropyl)methanol, 3,4,5,6,6-pentamethylheptan-2-ol, (E)-2-ethyl-4-(2,2,3-trimethylcyclopent-3-en-1-yl)but-2-en-1-ol, 3-methyl-5-(2,2,3-trimethylcyclopent-3-en-1-yl)pentan-2-ol, or mixtures thereof |
| 95 Woody-Vetiver | vetiver oil |

Example 3: Lack of Correlation Between Well-being Perception and Liking/Strength In order to confirm that the impact on well-being is not coupled to liking and/or strength of the test perfume compositions, a principal component analysis was performed on the panellists' individual ratings of liking and strength (Example 1, Section B), and well-being score (Example 1, Section C). The corresponding correlation coefficients are reported in Table 7:

TABLE 7

Correlation matrix relating perfume liking, perfume strength and well-being score

|  | Liking | Intensity | Well-being |
| --- | --- | --- | --- |
| Liking | 1.0 | | |
| Strength | 0.21 | 1.0 | |
| Well-being | −0.05 | −0.07 | 1.0 |

As apparent from Table 7, the well-being score is neither correlated to the variations of the perfume liking from one panellist to another nor to the variation of perfume strength perception from one panellist to another.

The invention claimed is:

1. A method of preparing or optimizing a perfume composition which enhances the well-being of a human subject, the method comprising:
   a) having one or more human subject(s) assess their well-being in the absence of a test perfume composition by scoring a plurality of well-being attributes;
      i. wherein the well-being attributes include "not anxious", "not sad", "not restless", "not frustrated", "not stressed", "happy", "optimistic", "excited", "satisfied", "motivated", "invigorated", "interested", "not bored", "not fatigued", "mentally alert", "calm", "relaxed", and "patient"; and
      ii. wherein each well-being attribute has a weight;
   b) calculating a base well-being score in the absence of the test perfume composition by multiplying the score of each well-being attribute by the corresponding weight to form a product and summing these products over all well-being attributes;
   c) repeating a) and b) in the presence of the test perfume composition in order to determine a test well-being score with the test perfume composition;
   d) determining the impact of the test perfume composition on the well-being by subtracting the base well-being score from the test well-being score with the test perfume composition;
   e) selecting perfume compositions with a positive impact on the well-being based on the determined impact of the test perfume composition;
   f) comparing perfume ingredients present in the selected perfume compositions having a positive impact on the well-being;
   g) identifying odour attributes common to the selected perfume compositions based on the compared perfume ingredients; and
   h) creating a new perfume composition with an increased proportion of perfume ingredients with the odour attributes identified in g),
   wherein the weights of the well-being attributes are as follows:

| well-being attribute | weight |
| --- | --- |
| "not anxious" | 10.65% |
| "not sad" | 10.32% |
| "not restless" | 9.84% |
| "not frustrated" | 9.65% |
| "not stressed" | 7.54% |
| "happy" | 4.70% |
| "optimistic" | 4.61% |
| "excited" | 4.13% |
| "satisfied" | 3.91% |
| "motivated" | 3.34% |
| "invigorated" | 3.31% |
| "interested" | 6.12% |
| "not bored" | 5.88% |
| "not fatigued" | 4.59% |
| "mentally alert" | 4.41% |
| "calm" | 2.66% |
| "relaxed" | 2.24% |
| "patient" | 2.10%. |

2. The method of claim 1, wherein in step h), the proportion of one or more perfume ingredient(s) having odour attributes selected from the group consisting of "citrus-mandarin", "citrus-orange", "floral-orange flower", "animalic-fecal", "floral-medicinal", "fruity-candied fruit", "spicy-cinnamon", "sweet-tonka", "citrus-lime" and "spicy-clove" is increased.

* * * * *